United States Patent
Eckhardt et al.

(10) Patent No.: US 8,901,043 B2
(45) Date of Patent: Dec. 2, 2014

(54) SYSTEMS FOR AND METHODS OF HYBRID PYROSEQUENCING

(75) Inventors: Allen E. Eckhardt, Durham, NC (US); Jonathan Benton, Apex, NC (US); Deborah Boles, Cary, NC (US)

(73) Assignee: Advanced Liquid Logic, Inc., Research Triangle Park, NC (US)

( * ) Notice: Subject to any disclaimer, the term of this patent is extended or adjusted under 35 U.S.C. 154(b) by 0 days.

(21) Appl. No.: 13/542,721

(22) Filed: Jul. 6, 2012

(65) Prior Publication Data

US 2013/0178374 A1 Jul. 11, 2013

Related U.S. Application Data

(60) Provisional application No. 61/504,796, filed on Jul. 6, 2011.

(51) Int. Cl.
| | | |
|---|---|---|
| *C40B 30/00* | (2006.01) | |
| *C12N 15/10* | (2006.01) | |
| *C12Q 1/68* | (2006.01) | |
| *G06F 19/22* | (2011.01) | |
| *G06F 19/24* | (2011.01) | |

(52) U.S. Cl.
CPC .......... *C12N 15/1089* (2013.01); *C12Q 1/6869* (2013.01); *G06F 19/22* (2013.01); *G06F 19/24* (2013.01)
USPC ..................................... 506/7; 506/2; 435/6.1

(58) Field of Classification Search
None
See application file for complete search history.

(56) References Cited

U.S. PATENT DOCUMENTS

| | | | |
|---|---|---|---|
| 4,636,785 | A | 1/1987 | Le Pesant |
| 5,181,016 | A | 1/1993 | Lee et al. |
| 5,486,337 | A | 1/1996 | Ohkawa et al. |
| 6,063,339 | A | 5/2000 | Tisone et al. |
| 6,130,098 | A | 10/2000 | Handique et al. |
| 6,294,063 | B1 | 9/2001 | Becker et al. |
| 6,565,727 | B1 | 5/2003 | Shenderov |

(Continued)

FOREIGN PATENT DOCUMENTS

| | | | |
|---|---|---|---|
| WO | 0069565 | A1 | 11/2000 |
| WO | 0073655 | A1 | 12/2000 |

(Continued)

OTHER PUBLICATIONS

Pourmand et al. (2006) "Rapid and Highly Informative Diagnostic Assay for H5N1 Influenza Viruses" PLoS One 1(1): e95.*

(Continued)

*Primary Examiner* — Tracy Vivlemore
*Assistant Examiner* — Karen S Weiler
(74) *Attorney, Agent, or Firm* — William A. Barrett; Ward & Smith, P.A.

(57) ABSTRACT

The systems and methods of the invention provide a guided approach to pyrosequencing (i.e., hybrid pyrosequencing). A de novo nucleic acid sequence may compared to a library of possible results and the next nucleotide to be dispensed is selected based on the comparison of the de novo sequence and the library of possible results. In another example, at least the first nucleotide to be dispensed is selected based on a query of a database(s) of non-sequence parameters (e.g., incidence of infection, diagnostic symptoms, sample source) and subsequent dispensations determined based on a comparison of the de novo sequence and the library of possible results (e.g., candidate sequences). The systems and methods of the invention may be performed using a droplet actuator.

19 Claims, 4 Drawing Sheets

(56) References Cited

U.S. PATENT DOCUMENTS

| | | | |
|---|---|---|---|
| 6,773,566 B2 | 8/2004 | Shenderov |
| 6,790,011 B1 | 9/2004 | Le Pesant et al. |
| 6,911,132 B2 | 6/2005 | Pamula et al. |
| 6,924,792 B1 | 8/2005 | Jessop |
| 6,977,033 B2 | 12/2005 | Becker et al. |
| 6,989,234 B2 | 1/2006 | Kolar et al. |
| 7,052,244 B2 | 5/2006 | Fouillet et al. |
| 7,163,612 B2 | 1/2007 | Sterling et al. |
| 7,211,223 B2 | 5/2007 | Fouillet et al. |
| 7,255,780 B2 | 8/2007 | Shenderov |
| 7,328,979 B2 | 2/2008 | Decre et al. |
| 7,329,545 B2 | 2/2008 | Pamula et al. |
| 7,439,014 B2 | 10/2008 | Pamula et al. |
| 7,458,661 B2 | 12/2008 | Kim et al. |
| 7,531,072 B2 | 5/2009 | Roux et al. |
| 7,547,380 B2 | 6/2009 | Velev |
| 7,569,129 B2 | 8/2009 | Pamula et al. |
| 7,641,779 B2 | 1/2010 | Becker et al. |
| 7,727,466 B2 | 6/2010 | Meathrel et al. |
| 7,727,723 B2 * | 6/2010 | Pollack et al. ............... 435/6.11 |
| 7,759,132 B2 | 7/2010 | Pollack et al. |
| 7,763,471 B2 | 7/2010 | Pamula et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,875,160 B2 | 1/2011 | Jary |
| 7,901,947 B2 | 3/2011 | Pollack et al. |
| 7,919,330 B2 | 4/2011 | De Guzman et al. |
| 7,922,886 B2 | 4/2011 | Fouillet et al. |
| 7,939,021 B2 | 5/2011 | Smith et al. |
| 7,943,030 B2 | 5/2011 | Shenderov |
| 7,989,056 B2 | 8/2011 | Plissonier et al. |
| 7,998,436 B2 | 8/2011 | Pollack |
| 8,007,739 B2 | 8/2011 | Pollack et al. |
| 8,041,463 B2 | 10/2011 | Pollack et al. |
| 8,048,628 B2 | 11/2011 | Pollack et al. |
| 8,075,754 B2 | 12/2011 | Sauter-Starace et al. |
| 8,088,578 B2 | 1/2012 | Hua et al. |
| 8,093,062 B2 | 1/2012 | Winger et al. |
| 8,093,064 B2 | 1/2012 | Shah et al. |
| 8,137,917 B2 | 3/2012 | Pollack et al. |
| 8,147,668 B2 | 4/2012 | Pollack et al. |
| 8,202,686 B2 | 6/2012 | Pamula et al. |
| 8,208,146 B2 | 6/2012 | Srinivasan et al. |
| 8,221,605 B2 | 7/2012 | Pollack et al. |
| 8,236,156 B2 | 8/2012 | Sarrut et al. |
| 8,268,246 B2 | 9/2012 | Srinivasan et al. |
| 8,287,711 B2 | 10/2012 | Pollack et al. |
| 8,304,253 B2 | 11/2012 | Yi et al. |
| 8,313,698 B2 | 11/2012 | Pollack et al. |
| 8,317,990 B2 | 11/2012 | Pamula et al. |
| 8,342,207 B2 | 1/2013 | Raccurt et al. |
| 8,349,276 B2 | 1/2013 | Pamula et al. |
| 8,364,315 B2 | 1/2013 | Sturmer et al. |
| 8,388,909 B2 | 3/2013 | Pollack et al. |
| 8,389,297 B2 | 3/2013 | Pamula et al. |
| 8,394,249 B2 | 3/2013 | Pollack et al. |
| 8,394,641 B2 | 3/2013 | Winger |
| 8,426,213 B2 | 4/2013 | Eckhardt et al. |
| 8,440,392 B2 | 5/2013 | Pamula et al. |
| 8,444,836 B2 | 5/2013 | Fouillet et al. |
| 2002/0005354 A1 | 1/2002 | Spence et al. |
| 2002/0036139 A1 | 3/2002 | Becker et al. |
| 2002/0043463 A1 | 4/2002 | Shenderov |
| 2002/0058332 A1 | 5/2002 | Quake et al. |
| 2002/0143437 A1 | 10/2002 | Handique et al. |
| 2003/0164295 A1 | 9/2003 | Sterling |
| 2003/0183525 A1 | 10/2003 | Elrod et al. |
| 2003/0205632 A1 | 11/2003 | Kim et al. |
| 2004/0023209 A1 * | 2/2004 | Jonasson ............... 435/5 |
| 2004/0031688 A1 | 2/2004 | Shenderov |
| 2004/0055891 A1 | 3/2004 | Pamula et al. |
| 2004/0058450 A1 | 3/2004 | Pamula et al. |
| 2004/0231987 A1 | 11/2004 | Sterling et al. |
| 2006/0021875 A1 | 2/2006 | Griffith et al. |
| 2006/0054503 A1 | 3/2006 | Pamula et al. |
| 2006/0164490 A1 | 7/2006 | Kim et al. |
| 2006/0194331 A1 | 8/2006 | Pamula et al. |
| 2006/0231398 A1 | 10/2006 | Sarrut et al. |
| 2007/0023292 A1 | 2/2007 | Kim et al. |
| 2007/0037294 A1 | 2/2007 | Pamula et al. |
| 2007/0045117 A1 | 3/2007 | Pamula et al. |
| 2007/0064990 A1 | 3/2007 | Roth |
| 2007/0086927 A1 | 4/2007 | Natarajan et al. |
| 2007/0207513 A1 | 9/2007 | Sorensen et al. |
| 2007/0217956 A1 | 9/2007 | Pamula et al. |
| 2007/0241068 A1 | 10/2007 | Pamula et al. |
| 2007/0242105 A1 | 10/2007 | Srinivasan et al. |
| 2007/0242111 A1 | 10/2007 | Pamula et al. |
| 2007/0243634 A1 | 10/2007 | Pamula et al. |
| 2007/0267294 A1 | 11/2007 | Shenderov |
| 2007/0275415 A1 | 11/2007 | Srinivasan et al. |
| 2008/0006535 A1 | 1/2008 | Paik et al. |
| 2008/0038810 A1 | 2/2008 | Pollack et al. |
| 2008/0044893 A1 | 2/2008 | Pollack et al. |
| 2008/0044914 A1 | 2/2008 | Pamula et al. |
| 2008/0050834 A1 | 2/2008 | Pamula et al. |
| 2008/0053205 A1 | 3/2008 | Pollack et al. |
| 2008/0105549 A1 | 5/2008 | Pamela et al. |
| 2008/0124252 A1 | 5/2008 | Marchand et al. |
| 2008/0142376 A1 | 6/2008 | Fouillet et al. |
| 2008/0151240 A1 | 6/2008 | Roth |
| 2008/0210558 A1 | 9/2008 | Sauter-Starace et al. |
| 2008/0247920 A1 | 10/2008 | Pollack et al. |
| 2008/0264797 A1 | 10/2008 | Pamula et al. |
| 2008/0274513 A1 | 11/2008 | Shenderov et al. |
| 2008/0281471 A1 | 11/2008 | Smith et al. |
| 2008/0283414 A1 | 11/2008 | Monroe et al. |
| 2008/0302431 A1 | 12/2008 | Marchand et al. |
| 2008/0305481 A1 | 12/2008 | Whitman et al. |
| 2009/0014394 A1 | 1/2009 | Yi et al. |
| 2009/0042319 A1 | 2/2009 | De Guzman et al. |
| 2009/0127123 A1 | 5/2009 | Raccurt et al. |
| 2009/0134027 A1 | 5/2009 | Jary |
| 2009/0142564 A1 | 6/2009 | Plissonnier et al. |
| 2009/0150084 A1 * | 6/2009 | Colwell et al. ............... 702/20 |
| 2009/0155902 A1 | 6/2009 | Pollack et al. |
| 2009/0192044 A1 | 7/2009 | Fouillet |
| 2009/0260988 A1 | 10/2009 | Pamula et al. |
| 2009/0263834 A1 | 10/2009 | Sista et al. |
| 2009/0280251 A1 | 11/2009 | De Guzman et al. |
| 2009/0280475 A1 | 11/2009 | Pollack et al. |
| 2009/0280476 A1 | 11/2009 | Srinivasan et al. |
| 2009/0283407 A1 | 11/2009 | Shah et al. |
| 2009/0288710 A1 | 11/2009 | Viovy et al. |
| 2009/0291433 A1 | 11/2009 | Pollack et al. |
| 2009/0304944 A1 | 12/2009 | Sudarsan et al. |
| 2009/0311713 A1 | 12/2009 | Pollack et al. |
| 2009/0321262 A1 | 12/2009 | Adachi et al. |
| 2010/0025242 A1 | 2/2010 | Pamula et al. |
| 2010/0025250 A1 | 2/2010 | Pamula et al. |
| 2010/0028920 A1 | 2/2010 | Eckhardt |
| 2010/0032293 A1 | 2/2010 | Pollack et al. |
| 2010/0041086 A1 | 2/2010 | Pamula et al. |
| 2010/0048410 A1 | 2/2010 | Shenderov et al. |
| 2010/0062508 A1 | 3/2010 | Pamula et al. |
| 2010/0068764 A1 | 3/2010 | Sista et al. |
| 2010/0087012 A1 | 4/2010 | Shenderov et al. |
| 2010/0096266 A1 | 4/2010 | Kim et al. |
| 2010/0116640 A1 | 5/2010 | Pamula et al. |
| 2010/0118307 A1 | 5/2010 | Srinivasan et al. |
| 2010/0120130 A1 | 5/2010 | Srinivasan et al. |
| 2010/0126860 A1 | 5/2010 | Srinivasan et al. |
| 2010/0130369 A1 | 5/2010 | Shenderov et al. |
| 2010/0140093 A1 | 6/2010 | Pamula et al. |
| 2010/0143963 A1 | 6/2010 | Pollack |
| 2010/0151439 A1 | 6/2010 | Pamula et al. |
| 2010/0190263 A1 | 7/2010 | Srinivasan et al. |
| 2010/0194408 A1 | 8/2010 | Sturmer et al. |
| 2010/0221713 A1 | 9/2010 | Pollack et al. |
| 2010/0236927 A1 | 9/2010 | Pope et al. |
| 2010/0236928 A1 | 9/2010 | Srinivasan et al. |
| 2010/0236929 A1 | 9/2010 | Pollack et al. |

(56) References Cited

U.S. PATENT DOCUMENTS

| | | |
|---|---|---|
| 2010/0258441 A1 | 10/2010 | Sista et al. |
| 2010/0270156 A1 | 10/2010 | Srinivasan et al. |
| 2010/0279374 A1 | 11/2010 | Sista et al. |
| 2010/0282608 A1 | 11/2010 | Srinivasan et al. |
| 2010/0282609 A1 | 11/2010 | Pollack et al. |
| 2010/0307917 A1 | 12/2010 | Srinivasan et al. |
| 2010/0320088 A1 | 12/2010 | Fouillet et al. |
| 2010/0323405 A1 | 12/2010 | Pollack et al. |
| 2011/0076692 A1 | 3/2011 | Sista et al. |
| 2011/0086377 A1 | 4/2011 | Thwar et al. |
| 2011/0091989 A1 | 4/2011 | Sista et al. |
| 2011/0097763 A1 | 4/2011 | Pollack et al. |
| 2011/0100823 A1 | 5/2011 | Pollack et al. |
| 2011/0104725 A1 | 5/2011 | Pamula et al. |
| 2011/0104747 A1 | 5/2011 | Pollack et al. |
| 2011/0104816 A1 | 5/2011 | Pollack et al. |
| 2011/0114490 A1 | 5/2011 | Pamula et al. |
| 2011/0118132 A1 | 5/2011 | Winger et al. |
| 2011/0147215 A1 | 6/2011 | Fuchs et al. |
| 2011/0180571 A1 | 7/2011 | Srinivasan et al. |
| 2011/0186433 A1 | 8/2011 | Pollack et al. |
| 2011/0203930 A1 | 8/2011 | Pamula et al. |
| 2011/0209998 A1 | 9/2011 | Shenderov |
| 2011/0213499 A1 | 9/2011 | Sturmer et al. |
| 2011/0303542 A1 | 12/2011 | Srinivasan et al. |
| 2011/0311980 A1 | 12/2011 | Pollack et al. |
| 2012/0018306 A1 | 1/2012 | Srinivasan et al. |
| 2012/0044299 A1 | 2/2012 | Winger |
| 2012/0132528 A1 | 5/2012 | Shenderov et al. |
| 2012/0136147 A1 | 5/2012 | Winger |
| 2012/0165238 A1 | 6/2012 | Pamula et al. |
| 2013/0059366 A1 | 3/2013 | Pollack et al. |

FOREIGN PATENT DOCUMENTS

| | | |
|---|---|---|
| WO | 2004029585 A1 | 4/2004 |
| WO | 2004030820 | 4/2004 |
| WO | 2005047696 A1 | 5/2004 |
| WO | 2006013303 A1 | 2/2006 |
| WO | 2006070162 A1 | 7/2006 |
| WO | 2006081558 | 8/2006 |
| WO | 2006124458 A2 | 11/2006 |
| WO | 2006127451 A2 | 11/2006 |
| WO | 2006134307 A1 | 12/2006 |
| WO | 2006138543 | 12/2006 |
| WO | 2007003720 A1 | 1/2007 |
| WO | 2007012638 A1 | 2/2007 |
| WO | 2007033990 A1 | 3/2007 |
| WO | 2007048111 | 4/2007 |
| WO | 2007120240 A2 | 10/2007 |
| WO | 2007120241 A2 | 10/2007 |
| WO | 2007123908 A2 | 11/2007 |
| WO | 2008051310 A2 | 5/2008 |
| WO | 2008055256 A3 | 5/2008 |
| WO | 2008068229 A1 | 6/2008 |
| WO | 2008091848 A2 | 7/2008 |
| WO | 2008098236 A2 | 8/2008 |
| WO | 2008101194 A2 | 8/2008 |
| WO | 2008106678 A1 | 9/2008 |
| WO | 2008109664 A1 | 9/2008 |
| WO | 2008112856 A1 | 9/2008 |
| WO | 2008116209 A1 | 9/2008 |
| WO | 2008116221 A1 | 9/2008 |
| WO | 2008118831 A2 | 10/2008 |
| WO | 2008124846 A2 | 10/2008 |
| WO | 2008131420 A2 | 10/2008 |
| WO | 2008134153 A1 | 11/2008 |
| WO | 2009002920 A1 | 12/2008 |
| WO | 2009003184 A1 | 12/2008 |
| WO | 2009011952 A1 | 1/2009 |
| WO | 2009021173 A1 | 2/2009 |
| WO | 2009021233 A2 | 2/2009 |
| WO | 2009026339 A2 | 2/2009 |
| WO | 2009029561 A2 | 3/2009 |
| WO | 2009032863 A2 | 3/2009 |
| WO | 2009052095 A1 | 4/2009 |
| WO | 2009052123 A2 | 4/2009 |
| WO | 2009052321 A2 | 4/2009 |
| WO | 2009052345 | 4/2009 |
| WO | 2009052348 A2 | 4/2009 |
| WO | 2009076414 | 6/2009 |
| WO | 2009086403 A2 | 7/2009 |
| WO | 2009111769 A2 | 9/2009 |
| WO | 2009135205 A2 | 11/2009 |
| WO | 2009137415 A2 | 11/2009 |
| WO | 2009140373 A2 | 11/2009 |
| WO | 2009140671 A2 | 11/2009 |
| WO | 2010004014 A1 | 1/2010 |
| WO | 2010006166 A2 | 1/2010 |
| WO | 2010009463 A2 | 1/2010 |
| WO | 2010019782 A2 | 2/2010 |
| WO | 2010027894 A2 | 3/2010 |
| WO | 2010042637 A2 | 4/2010 |
| WO | 2010077859 A3 | 7/2010 |
| WO | 2011002957 A2 | 1/2011 |
| WO | 2011020011 A2 | 2/2011 |
| WO | 2011057197 A2 | 5/2011 |
| WO | 2011084703 A2 | 7/2011 |
| WO | 2011126892 A2 | 10/2011 |
| WO | 2012009320 A2 | 1/2012 |
| WO | 2012012090 A2 | 1/2012 |
| WO | 2012037308 A2 | 3/2012 |
| WO | 2012068055 A3 | 5/2012 |

OTHER PUBLICATIONS

Edlund et al. (2009) "Y chromosomal STR analysis using Pyrosequencing technology" Forensic Science International: Genetics 3(2):119-124.*

Benton et al., "Library Preparation Method 1 DNA Library Construction for Illumina SBS Sequencing Platforms using NEBNext® Library Preparation Reagents", Application Note, NuGEN, 2011.

Bottausci et al., "Fully Integrated EWOD Based Bio-Analysis Device", Labautomation 2011, Palm Springs Convention Center, Palm Springs, CA, USA; Abstract in Proceedings on line, poster distributed, Jan. 29-Feb. 2, 2011.

Burde et al., "Digital Microfluidic Rapid HIV Point-of-Care Diagnostic Device for Resource Limited Settings", Workshop on TB and HIV Diagnostics, Silver Spring, MD. (Poster, copies distributed to attendees.) http://www.blsmeetings.net/TB-HIV-Dx-Wkshop/index.cfm, Jun. 28, 2011.

Burton et al., "Diagnosis of Fabry and Gaucher diseases from the Pilot Screening of Newborns for Lysosomal Storage Disorders in Illinois", APHL Newborn Screening and Genetic Testing Symposium, San Diego, 2011.

Chakrabarty, "Automated Design of Microfluidics-Based Biochips: connecting Biochemistry of Electronics CAD", IEEE International Conference on Computer Design, San Jose, CA, Oct. 1-4, 2006, 93-100.

Chakrabarty et al., "Design Automation Challenges for Microfluidics-Based Biochips", DTIP of MEMS & MOEMS, Montreux, Switzerland, Jun. 1-3, 2005.

Chakrabarty et al., "Design Automation for Microfluidics-Based Biochips", ACM Journal on Engineering Technologies in Computing Systems , 1(3), Oct. 2005, 186-223.

Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.

Chen et al., "Development of Mesoscale Actuator Device with Micro Interlocking Mechanism", J. Intelligent Material Systems and Structures, vol. 9, No. 4, Jun. 1998, pp. 449-457.

Chen et al., "Mesoscale Actuator Device with Micro Interlocking Mechanism", Proc. IEEE Micro Electro Mechanical Systems Workshop, Heidelberg, Germany, Jan. 1998, pp. 384-389.

Chen et al., "Mesoscale Actuator Device: Micro Interlocking Mechanism to Transfer Macro Load", Sensors and Actuators, vol. 73, Issues 1-2, Mar. 1999, pp. 30-36.

(56) References Cited

OTHER PUBLICATIONS

Cotten et al., "Digital Microfluidics: a novel platform for multiplexed detection of lysosomal storage diseases", Abstract #3747.9. Pediatric Academic Society Conference, 2008.

Delapierre et al., "SmartDrop: An Integrated System from Sample Collection to Result using real-time PCR", 4th National Bio-Threat Conference, New Orleans, LA, USA; Poster presented at conference., Dec. 7-9, 2010.

Delattre et al., "SmartDrop: an integrated system from sample preparation to analysis using real-time PCR", 10th International Symposium on Protection against Chemical and Biological Warfare Agents; Stockholm, Sweden; poster, Jun. 10, 2010.

Delattre et al., "SmartDrop: An integrated system from sample preparation to analysis using real-time PCR", 10th International Symposium on Protection against Chemical and Biological Warfare Agents; Stockholm, Sweden; Abstract,paper,, Jun. 8-11, 2010.

Delattre et al., "Towards an industrial fabrication process for electrowetting chip using standard MEMS Technology", μTAS2008, San Diego; poster presented, Oct. 15, 2008.

Delattre et al., "Towards an industrial fabrication process for electrowetting chip using standard MEMS Technology", μTAS2008, San Diego; Abstract in proceedings, Oct. 13-16, 2008, 1696-1698.

Dewey, "Towards a Visual Modeling Approach to Designing Microelectromechanical System Transducers", Journal of Micromechanics and Microengineering, vol. 9, Dec. 1999, 332-340.

Dewey et al., "Visual modeling and design of microelectromechanical system tansducers", Microelectronics Journal, vol. 32, Apr. 2001, 373-381.

Eckhardt et al., "Development and validation of a single-step fluorometric assay for Hunter syndrome", APHL Newborn Screening and Genetic Testing Symposium, San Diego, 2011.

Emani et al., "Novel Microfluidic Platform for Point of Care Hypercoagulability Panel Testing", Circulation, vol. 122, 2010, A14693.

Fair et al., "A Micro-Watt Metal-Insulator-Solution-Transport (MIST) Device for Scalable Digital Bio-Microfluidic Systems", IEEE IEDM Technical Digest, 2001, 16.4.1-4.

Fair et al., "Advances in droplet-based bio lab-on-a-chip", BioChips 2003, Boston, 2003.

Fair et al., "Bead-Based and Solution-Based Assays Performed on a Digital Microfluidic Platform", Biomedical Engineering Society (BMES) Fall Meeting, Baltimore, MD, Oct. 1, 2005.

Fair, "Biomedical Applications of Electrowetting Systems", 5th International Electrowetting Workshop, Rochester, NY, May 31, 2006.

Fair et al., "Chemical and Biological Applications of Digital-Microfluidic Devices", IEEE Design & Test of Computers, vol. 24(1), Jan.-Feb. 2007, 10-24.

Fair et al., "Chemical and biological pathogen detection in a digital microfluidic platform", DARPA Workshop on Microfluidic Analyzers for DoD and National Security Applications, Keystone, CO, 2006.

Fair, "Digital microfluidics: is a true lab-on-a-chip possible?", Microfluid Nanofluid, vol. 3, Mar. 8, 2007, 245-281.

Fair, "Droplet-based microfluidic Genome sequencing", NHGRI PI's meeting, Boston, 2005.

Fair et al., "Electrowetting-based On-Chip Sample Processing for Integrated Microfluidics", IEEE Inter. Electron Devices Meeting (IEDM), 2003, 32.5.1-32.5.4.

Fair et al., "Integrated chemical/biochemical sample collection, pre-concentration, and analysis on a digital microfluidic lab-on-a-chip platform", Lab-on-a-Chip: Platforms, Devices, and Applications, Conf. 5591, SPIE Optics East, Philadelphia, Oct. 25-28, 2004.

Fair, "Scaling of Digital Microfluidic Devices for Picoliter Applications", The 6th International Electrowetting Meeting, Aug. 20-22, 2008, p. 14.

Fouillet, "Bio-Protocol Integration in Digital Microfluidic Chips", The 6th International Electrowetting Meeting, Aug. 20-22, 2008, p. 15.

Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.

Fouillet et al., "Digital microfluidic design and optimization of classic and new fluidic functions for lab on a chip systems", Microfluid Nanofluid, vol. 4, 2008, 159-165.

Graham et al., "Development of Quality Control Spots for Lysosomal Storage Disorders under cGMP", APHL Newborn Screening and Genetic Testing Symposium, San Diego, 2011.

Hua et al., "Multiplexed real-time polymerase chain reaction on a digital microfluidic platform", Analytical Chemistry, vol. 82, No. 6, Mar. 15, 2010, Published on Web, Feb. 12, 2010, 2310-2316.

Hua et al., "Rapid Detection of Methicillin-Resistant Staphylococcus Aureus (MRSA) Using Digital Microfluidics", 12th Intl Conference on Miniaturized Systems for Chemistry and Life Sciences, Proc. μTAS, Oct. 12-16, 2008.

Jary et al., "Development of complete analytical system for Environment and homeland security", 14th International Conference on Biodetection Technologies 2009, Technological Responses to Biological Threats, Baltimore, MD; Abstract in Proceedings, poster distributed at conference, Jun. 25-26, 2009, 663.

Jary et al., "SmartDrop, Microfluidics for Biology", Forum 4i 2009, Grenoble, France; Flyer distributed at booth, May 14, 2009.

Jinks et al., "Newborn Screening for Krabbe and other Lysosomal Storage Diseases", The 3rd Annual Workshop on Krabbe Disease, Java Center, New York, Jul. 19-21, 2010, (Oral Presentation—No Abstract).

Jun et al., "Valveless Pumping using Traversing Vapor Bubbles in Microchannels", J. Applied Physics, vol. 83, No. 11, Jun. 1998, pp. 5658-5664.

Kim et al., "MEMS Devices Based on the Use of Surface Tension", Proc. Int. Semiconductor Device Research Symposium (ISDRS'99), Charlottesville, VA, Dec. 1999, pp. 481-484.

Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.

Kim et al., "Micromachines Driven by Surface Tension", AIAA 99-3800, 30th AIAA Fluid Dynamics Conference, Norfolk, VA, (Invited lecture), Jun. 1999, pp. 1-6.

Kleinert et al., "Electric Field Assisted Convective Assembly of Colloidal Crystal Coatings", Symposium MM: Evaporative Self Assembly of Polymers, Nanoparticles, and DNA, 2010 MRS Spring Meeting, San Francisco, CA., Apr. 6-8, 2010.

Kleinert et al., "Electric Field-Assisted Convective Assembly of Large-Domain Colloidal Crystals", The 82nd Colloid & Surface Science Symposium, ACS Division of Colloid & Surface Science, North Carolina State University, Raleigh, NC. www.colloids2008.org., Jun. 15-18, 2008.

Kleinert, "Electric-Field-Assisted Convective Assembly of Colloidal Crystal Coatings", Langmuir, vol. 26(12), May 13, 2010, 10380-10385.

Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.

Lee et al., "Liquid Micromotor Driven by Continuous Electrowetting", Proc. IEEE Micro Electro Mechanical Systems Workshop, Heidelberg, Germany, Jan. 1998, pp. 538-543.

Lee et al., "Theory and Modeling of Continuous Electrowetting Microactuation", Proc. MEMS (MEMS—vol. 1), ASME Int. Mechanical Engineering Congress and Exposition, Nashville, TN, Nov. 1999, pp. 397-403.

Malk et al., "EWOD in coplanar electrode configurations", Proceedings of ASME 2010 3rd Joint US-European Fluids Engineering Summer Meeting and 8th International Conference on Nanochannels, Microchannels, and Minichannels, http://asmedl.org/getabs/servlet/GetabsServlet?prog=normal&id=ASMECP002010054501000239000000, Aug. 1-5, 2010.

Marchand et al., "Organic Synthesis in Soft Wall-Free Microreactors: Real-Time Monitoring of Fluorogenic Reactions", Analytical Chemistry, vol. 80, Jul. 2, 2008, 6051-6055.

(56) References Cited

OTHER PUBLICATIONS

Millington et al., "Digital microfluidics: a future technology in the newborn screening laboratory", Seminars in Perinatology, vol. 34, Apr. 2010, 163-169.

Millington et al., "Digital Microfluidics: a novel platform for multiplexed detection of LSDs with potential for newborn screening", Association of Public Health Laboratories Annual Conference, San Antonio, TX, Nov 4, 2008.

Millington et al., "Digital Microfluidics: A Novel Platform for Multiplexing Assays Used in Newborn Screening", Proceedings of the 7th International and Latin American Congress. Oral Presentations. Rev Invest Clin; vol. 61 (Supl. 1), 2009, 21-33.

Paik et al., "A digital-microfluidic approach to chip cooling", IEEE Design & Test of Computers, vol. 25, Jul. 2008, 372-381.

Paik et al., "Adaptive Cooling of Integrated Circuits Using Digital Microfluidics", IEEE Transactions on VLSI, vol. 16, No. 4, 2008, 432-443.

Paik et al., "Adaptive Cooling of Integrated Circuits Using Digital Microfluidics", accepted for publication in IEEE Transactions on VLSI Systems, 2007, and Artech House, Norwood, MA, 2007.

Paik, "Adaptive Hot-Spot Cooling of Integrated Circuits Using Digital Microfluidics", Dissertation, Dept. of Electrical and Computer Engineering, Duke University, Apr. 25, 2006, 1-188.

Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.

Paik et al., "Coplanar Digital Microfluidics Using Standard Printed Circuit Board Processes", 9th International Conference on Miniaturized Systems for Chemistry and Life Sciences (MicroTAS), Boston, MA; Poster, 2005.

Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.

Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.

Paik et al., "Electrowetting-based droplet mixers for microfluidic systems", Lab on a Chip (LOC), vol. 3. (more mixing videos available, along with the article, at LOC's website), 2003, 28-33.

Paik et al., "Programmable Flow-Through Real Time PCR Using Digital Microfluidics", 11th International Conference on Miniaturized Systems for Chemistry and Life Sciences, Paris, France, Oct. 7-11, 2007, 1559-1561.

Paik et al., "Programmable flow-through real-time PCR using digital microfluidics", Proc. Micro Total Analysis Systems (μTAS), Handout, 2007.

Paik et al., "Programmable flow-through real-time PCR using digital microfluidics", Proc. Micro Total Analysis Systems (μTAS), Poster, 2007.

Paik et al., "Rapid Droplet Mixers for Digital Microfluidic Systems", Masters Thesis, Duke Graduate School., 2002, 1-82.

Paik et al., "Rapid droplet mixers for digital microfluidic systems", Lab on a Chip, vol. 3. (More mixing videos available, along with the article, at LOC's website.), 2003, 253-259.

Paik et al., "Thermal effects on Droplet Transport in Digital Microfluids with Application to Chip Cooling Processing for Integrated Microfluidics", International Conference on Thermal, Mechanics, and Thermomechanical Phenomena in Electronic Systems (ITherm), 2004, 649-654.

Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.

Pamula et al., "A droplet-based lab-on-a-chip for colorimetric detection of nitroaromatic explosives", Proceedings of Micro Electro Mechanical Systems, 2005, 722-725.

Pamula et al., "Cooling of integrated circuits using droplet-based microfluidics", Proc. ACM Great Lakes Symposium on VLSI, Apr. 2003, 84-87.

Pamula, "Digital microfluidic lab-on-a-chip for multiplexing tests in newborn screening", Newborn Screening Summit: Envisioning a Future for Newborn Screening, Bethesda, MD, Dec. 7, 2009.

Pamula et al., "Digital microfluidic lab-on-a-chip for protein crystallization", 5th Protein Structure Initiative "Bottlenecks" Workshop, NIH, Bethesda, MD, Apr. 13-14, 2006, I-16.

Pamula et al., "Digital Microfluidic Methods in Diagnosis of Neonatal Biochemical Abnormalities", Developing Safe and Effective Devices and Instruments for Use in the Neonatal Intensive Care for the 21st Century, Pediatric Academic Societies' Annual Meeting, Vancouver, Canada, May 1-4, 2010.

Pamula et al., "Digital Microfluidic Platform for Multiplexing LSD Assays in Newborn Screening", LSD World Meeting, Las Vegas, NV, Feb. 16-18, 2011.

Pamula et al., "Digital Microfluidics Platform for Lab-on-a-chip applications", Duke University Annual Post Doctoral Research Day, 2002.

Pamula et al., "Microfluidic electrowetting-based droplet mixing", IEEE, 2002, 8-10.

Pamula, "Sample Preparation and Processing using Magnetic Beads on a Digital Microfluidic Platform", CHI's Genomic Sample Prep, San Francisco, CA, Jun. 9-10, 2009.

Pamula, "Sample-to-sequence-molecular diagnostics on a digital microfluidic lab on a chip", Pre-conference workshops, 4th International Conference on Birth Defects and Disabilities in the Developing World, New Dehli, India, Oct. 4, 2009.

Pamula et al. (CO-CHAIR, "Digital Microfluidics for Lab-on-a-Chip Applications", "Emerging CAD Challenges for Biochip Design" Workshop, Conference on Design, Automation, and Test in Europe (Date), Munich, Germany, Advance Programme, 2006, pp. 85-87.

Pollack et al., "Applications of Electrowetting-Based Digital Microfluidics in Clinical Diagnostics", Expert Rev. Mol. Diagn., vol. 11(4), 2011, 393-407.

Pollack et al., "Continuous sequencing-by-synthesis-based on a digital microfluidic platform", National Human Genome Research Institute, Advanced DNA Sequencing Technology Development Meeting, Chapel Hill, NC, Mar. 10-11, 2010.

Pollack, et al., "Electrowetting-Based Actuation of Droplets for Integrated Microfluidics", Lab on a Chip (LOC), vol. 2, 2002, 96-101.

Pollack et al., "Electrowetting-based actuation of liquid droplets for microfluidic applications", Appl. Phys. Letters, vol. 77, No. 11, Sep. 11, 2000, 1725-1726.

Pollack, "Electrowetting-based Microactuation of Droplets for Digital Microfluidics", PhD Thesis, Department of Electrical and Computer Engineering, Duke University, 2001.

Pollack et al., "Electrowetting-Based Microfluidics for High-Throughput Screening", smallTalk 2001 Conference Program Abstract, San Diego, Aug. 27-31, 2001, 149.

Pollack et al., "Investigation of electrowetting-based microfluidics for real-time PCR applications", Proc. 7th Int'l Conference on Micro Total Analysis Systems (mTAS), Squaw Valley, CA, Oct. 5-9, 2003, 619-622.

Pollack, "Lab-on-a-chip platform based digital microfluidics", The 6th International Electrowetting Meeting, Aug. 20-22, 2008, 16.

Punnamaraju, "Voltage and Photo Induced Effects in Droplet-Interface-Bilayer Lipid", PhD Thesis, University of Cincinnati, 2011.

Punnamaraju et al., "Voltage Control of Droplet Interface Bilayer Lipid Membrane Dimensions", Langmuir the ACS Journal of Surfaces and Colloids, vol. 27, Issue 2, 2011, Published on Web, Dec. 10, 2010, 618-626.

Ren et al., "Automated electrowetting-based droplet dispensing with good reproducibility", Proc. Micro Total Analysis Systems (mTAS), 7th Int. Conf. on Miniaturized Chem and Biochem Analysis Systems, Squaw Valley, CA, Oct. 5-9, 2003, 993-996.

Ren et al., "Automated on-chip droplet dispensing with volume control by electro-wetting actuation and capacitance metering", Sensors and Actuators B: Chemical, vol. 98, Mar. 2004, 319-327.

Ren et al., "Design and testing of an interpolating mixing architecture for electrowetting-based droplet-on-chip chemical dilution", Trans-

(56) References Cited

OTHER PUBLICATIONS ducers, 12th International Conference on Solid-State Sensors, Actuators and Microsystems, 2003, 619-622.

Ren et al., "Dynamics of electro-wetting droplet transport", Sensors and Actuators B (Chemical), vol. B87, No. 1, Nov. 15, 2002, 201-206.

Ren et al., "Micro/Nano Liter Droplet Formation and Dispensing by Capacitance Metering and Electrowetting Actuation", IEEE-NANO, 2002, 369-372.

Rival et al., "EWOD Digital Microfluidic Device for Single Cells Sample Preparation and Gene Expression Analysis", Lab Automation 2010, Palm Springs Convention Center, Palm Springs, CA, USA; Abstract in Proceedings, Poster distributed at conference, Jan. 23-27, 2010.

Rival et al., "Expression de gènes de quelques cellules sur puce EWOD/Gene expression of few cells on EWOD chip", iRTSV,http://www-dsv.cea.fr/var/plain/storage/original/media/File/iRTSV/thema_08(2).pdf (english translation), Winter 2009-2010.

Rival et al., "Towards Single Cells Gene Expression on EWOD Lab on Chip", ESONN 2008, Grenoble, France; Poster presented, Aug. 26, 2008.

Rival et al., "Towards single cells gene expression on EWOD lab on chip", ESONN, Grenoble, France, abstract in proceedings, Aug. 2008.

Rival et al., "Towards single cells gene expression preparation and analysis on ewod lab on chip", Nanobio Europe 2009, Poster distributed at conference, Jun. 16-18, 2009.

Rival et al., "Towards single cells gene expression preparation and analysis on ewod lab on chip", Nanobio Europe 2009, Abstract in proceedings, Jun. 16-18, 2009.

Rival et al., "Towards single cells gene expression preparation and analysis on ewod lab on chip", Lab on Chip Europe 2009 poster distributed at Conference, May 19-20, 2009.

Rival et al., "Towards single cells gene expression preparation and analysis on ewod lab on chip", Lab on Chip Europe 2009, Abstract in proceedings, May 19-20, 2009.

Rouse et al., "Digital microfluidics: a novel platform for multiplexing assays used in newborn screening", Poster 47, 41st AACC's Annual Oak Ridge Conference Abstracts, Clinical Chemistry, vol. 55, 2009, 1891.

Sherman et al., "Flow Control by Using High-Aspect-Ratio, In-Plane Microactuators", Sensors and Actuators, vol. 73, 1999, pp. 169-175.

Sherman et al., "In-Plane Microactuator for Fluid Control Application", Proc. IEEE Micro Electro Mechanical Systems Workshop, Heidelberg, Germany, Jan. 1998, pp. 454-459.

Shi et al., "Evaluation of stability of fluorometric reagent kits for screening of Lysosomal Storage Disorders", APHL Newborn Screening and Genetic Testing Symposium, San Diego, 2011.

Sista et al., "96-Immunoassay Digital Microfluidic Multiwell Plate", Proc. μTAS, Oct. 12-16, 2008.

Sista, "Development of a Digital Microfluidic Lab-on-a-Chip for Automated Immunoassays with Magnetically Responsive Beads", PhD Thesis, Department of Chemical Engineering, Florida State University, 2007.

Sista et al., "Development of a digital microfluidic platform for point of care testing", Lab on a chip, vol. 8, Dec. 2008, First published as an Advance Article on the web, Nov. 5, 2008, 2091-2104.

Sista et al., "Digital Microfluidic platform for multiplexing LDS assays in newborn screening", APHL Newborn Screening and Genetic Testing Symposium, Orlando, May 3-6, 2010.

Sista et al., "Heterogeneous immunoassays using magnetic beads on a digital microfluidic platform", Lab on a Chip, vol. 8, Dec. 2008, First published as an Advance Article on the web, Oct. 14, 2008, 2188-2196.

Sista et al., "Performance of a digital microfluidic assay for Gaucher and Hurler disorders", APHL Newborn Screening and Genetic Testing Symposium, San Diego, 2011.

Sista et al., "Rapid, Single-Step Assay for Hunter Syndrome in Dried Blood Spots Using Digital Microfluidics", Clinica Chimica Acta, vol. 412, 2011, 1895-97.

Sista et al., "Spatial multiplexing of immunoassays for small-volume samples", 10th PI Meeting IMAT, Bethesda, 2009.

Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.

Srinivasan et al., "A digital microfluidic biosensor for multianalyte detection", Proc. IEEE 16th Annual Int'l Conf. on Micro Electro Mechanical Systems Conference, 2003, 327-330.

Srinivasan, "A Digital Microfluidic Lab-on-a-Chip for Clinical Diagnostic Applications", Ph.D. thesis, Dept of Electrical and Computer Engineering, Duke University, 2005.

Srinivasan et al., "An integrated digital microfluidic lab-on-a-chip for clinical diagnostics on human physiological fluids", Lab on a Chip, vol. 4, 2004, 310-315.

Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.

Srinivasan et al., "Digital Microfluidic Lab-on-a-Chip for Protein Crystallization", The 82nd ACS Colloid and Surface Science Symposium, 2008.

Srinivasan et al., "Digital Microfluidics: a novel platform for multiplexed detection of lysosomal storage diseases for newborn screening", AACC Oak Ridge Conference Abstracts, Clinical Chemistry, vol. 54, 2008, 1934.

Srinivasan et al., "Droplet-based microfluidic lab-on-a-chip for glucose detection", Analytica Chimica Acta, vol. 507, No. 1, 2004, 145-150.

Srinivasan et al., "Electrowetting", Chapter 5, Methods in Bioengineering: Biomicrofabrication and Biomicrofluidics, Ed. J.D. Zahn, ISBN: 9781596934009, Artech House Publishers, 2010.

Srinivasan et al., "Feasibility of a point of care newborn screening platform for hyperbilirubinemia", APHL Newborn Screening and Genetic Testing Symposium, San Diego, 2011.

Srinivasan et al., "Low cost digital microfluidic platform for protein crystallization", Enabling Technologies for Structural Biology, NIGMS Workshop, Bethesda, MD., Mar. 4-6, 2009, J-23.

Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.

Srinivasan et al., "Scalable Macromodels for Microelectromechanical Systems", Technical Proc. 2001 Int. Conf. on Modeling and Simulation of Microsystems, 2001, 72-75.

Su et al., "Yield Enhancement of Digital Microfluidics-Based Biochips Using Space Redundancy and Local Reconfiguration", Proc. Design, Automation and Test in Europe (Date) Conf., IEEE, 2005, 1196-1201.

Sudarsan et al., "Printed circuit technology for fabrication of plastic based microfluidic devices", Analytical Chemistry vol. 76, No. 11, Jun. 1, 2004, Previously published on-line, May 2004, 3229-3235.

Thwar et al., "DNA sequencing using digital microfluidics", Poster 42, 41st AACC's Annual Oak Ridge Conference Abstracts, Clinical Chemistry vol. 55, 2009, 1891.

Wang et al., "Comparison of enzyme activities for Pompe, Fabry, and Gaucher diseases on CDC's Quality Control spots between microplate fluorometry, mass spectrometry, and digital microfluidic fluorometry", APHL Newborn Screening and Genetic Testing Symposium, San Diego, 2011.

Wang et al., "Droplet-based micro oscillating-flow PCR chip", J. Micromechanics and Microengineering, vol. 15, 2005, 1369-1377.

Wang et al., "Efficient in-droplet separation of magnetic particles for digital microfluidics", Journal of Micromechanics and Microengineering, vol. 17, 2007, 2148-2156.

Wulff-Burchfield et al., "Microfluidic platform versus conventional real-time polymerase chain reaction for the detection of *Mycoplasma pneumoniae* in respiratory specimens", Diagnostic Microbiology and Infectious Disease, vol. 67, 2010, 22-29.

Xu et al., "A Cross-Referencing-Based Droplet Manipulation Method for High-Throughput and Pin-Constrained Digital Microfluidic Arrays", Proceedings of conference on Design, Automation and Test in Europe (Date ), Apr. 2007.

(56) References Cited

OTHER PUBLICATIONS

Xu et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.

Xu et al., "Automated solution preparation on a digital microfluidic lab-on-chip", PSI Bottlenecks Workshop, 2008.

Xu et al., "Automated, Accurate and Inexpensive Solution-Preparation on a Digital Microfluidic Biochip", Proc. IEEE Biomedical Circuits and Systems Conference (BioCAS), 2008, 301-304.

Xu et al., "Defect-Aware Synthesis of Droplet-Based Microfluidic Biochips", IEEE, 20th International Conference on VLSI Design, 2007.

Xu et al., "Defect-Tolerant Design and Optimization of a Digital Microfluidic Biochip for Protein Crystallization", IEEE Transactions on Computer Aided Design, vol. 29, No. 4, 2010, 552-565.

Xu et al., "Design and Optimization of a Digital Microfluidic Biochip for Protein Crystallization", Proc. IEEE/ACM International Conference on Computer-Aided Design (ICCAD), Nov. 2008, 297-301.

Xu et al., "Digital Microfluidic Biochip Design for Protein Crystallization", IEEE-NIH Life Science Systems and Applications Workshop, Lisa, Bethesda, MD, Nov. 8-9, 2007, 140-143.

Xu et al., "Droplet-Trace-Based Array Partitioning and a Pin Assignment Algorithm for the Automated Design of Digital Microfluidic Biochips", Codes, 2006, 112-117.

Xu et al., "Integrated Droplet Routing in the Synthesis of Microfluidic Biochips", IEEE, 2007, 948-953.

Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.

Xu et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.

Yang et al., "Manipulation of droplets in microfluidic systems", Trends in Analytical Chemistry, vol. 29, Feb. 2010, 141-157.

Yao et al., "Spot Cooling Using Thermoelectric Microcooler", Proc. 18th Int. Thermoelectric Conf, Baltimore, VA, pp. 256-259, Aug. 1999.

Yi et al., "Channel-to-droplet extractions for on-chip sample preparation", Solid-State Sensor, Actuators and Microsystems Workshop (Hilton Head '06), Hilton Head Island, SC, Jun. 2006, 128-131.

Yi et al., "Characterization of electrowetting actuation on addressable single-side coplanar electrodes", Journal of Micromechanics and Microengineering, vol. 16.,Oct. 2006, 2053-2059.

Yi et al., "EWOD Actuation with Electrode-Free Cover Plate", Digest of Tech. papers,13th International Conference on Solid-State Sensors, Actuators and Microsystems (Transducers '05), Seoul, Korea, Jun. 5-9, 2005, 89-92.

Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.

Yi, "Soft Printing of Biological Liquids for Micro-arrays: Concept, Principle, Fabrication, and Demonstration", Ph.D. dissertation, UCLA, 2004.

Yi et al., "Soft Printing of Droplets Digitized by Electrowetting", Transducers 12th Int'l Conf. on Solid State Sensors, Actuators and Microsystems, Boston, Jun. 8-12, 2003, 1804-1807.

Yi et al., "Soft Printing of Droplets Pre-Metered by Electrowetting", Sensors and Actuators A: Physical, vol. 114, Jan. 2004, 347-354.

Zeng et al., "Actuation and Control of Droplets by Using Electrowetting-on-Dielectric", Chin. Phys. Lett., vol. 21(9), 2004, 1851-1854.

Zhao et al., "Droplet Manipulation and Microparticle Sampling on Perforated Microfilter Membranes", J. Micromech. Microeng., vol. 18, 2008, 1-11.

Zhao et al., "In-droplet particle separation by travelling wave dielectrophoresis (twDEP) and EWOD", Solid-State Sensor, Actuators and Microsystems Workshop (Hilton Head '06), Hilton Head Island, SC, Jun. 2006, 181-184.

Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.

Zhao et al., "Microparticle Concentration and Separation byTraveling-Wave Dielectrophoresis (twDEP) for Digital Microfluidics", J. Microelectromechanical Systems, vol. 16, No. 6, Dec. 2007, 1472-1481.

Zhao et al., "Synchronization of Concurrently-Implemented Fluidic Operations in Pin-Constrained Digital Microfluidic Biochips", VLSI Design, (Best Paper Award), 2010.

Boles et al., "Droplet-Based Pyrosequencing Using Digital Microfluidics," Analytical Chemistry, 83(22), 2011, pp. 8439-8447.

\* cited by examiner

SYSTEMS FOR AND METHODS OF HYBRID PYROSEQUENCING

1A GOVERNMENT INTEREST

This invention was made with government support under HG004354 awarded by National Institute of Health. The United States Government has certain rights in the invention.

1B CROSS REFERENCE TO RELATED APPLICATIONS

This application claims the benefit of U.S. provisional application No. 61/504,796 filed Jul. 6, 2011, the disclosure of which is hereby incorporated by reference in its entirety.

2 TECHNICAL FIELD

The present disclosure relates to methods for pyrosequencing.

3 BACKGROUND

A droplet actuator typically includes one or more substrates configured to form a surface or gap for conducting droplet operations. The one or more substrates establish a droplet operations surface or gap for conducting droplet operations and may also include electrodes arranged to conduct the droplet operations. The droplet operations substrate or the gap between the substrates may be coated or filled with a filler fluid that is immiscible with the liquid that forms the droplets.

Droplet actuators are used to conduct a variety of molecular protocols, such as amplification of nucleic acids and nucleic acid sequencing. Nucleic acid amplification and sequencing methods are used in a wide variety of settings, such as medical diagnostics and detection of sequence variations. Pyrosequencing is a sequencing-by-synthesis method in which a primed DNA template strand is sequentially exposed to one of four nucleotides in the presence of DNA polymerase. The nucleotides are sequentially added one by one according to a fixed order dependent on the template and pre-determined by the user. Consequently, the operator must enter the order of the nucleotides before the instrument analysis begins. Thus, the operator needs to know the sequence of the sample in order to be able to enter the dispensation order in advance. In certain instances, an optimal dispensation order may be difficult to determine or is not known. As a consequence, many unnecessary dispensations may be made where no nucleotides are incorporated. Unnecessary dispensations are a waste of time and resources and contribute to a decline in accuracy as the sequencing reaction progresses. Recent advances in pyrosequencing technology include methods for using sequence information in a database of alleles and adapting the dispensation order in real-time during the analysis. However, this approach is limited to statistical selection of the next nucleotide to add based only on nucleotide frequency in a database. Therefore, there is a need for improved pyrosequencing methods for rapid, accurate and efficient sequencing of nucleic acids.

4 DEFINITIONS

As used herein, the following terms have the meanings indicated.

"Activate," with reference to one or more electrodes, means affecting a change in the electrical state of the one or more electrodes which, in the presence of a droplet, results in a droplet operation. Activation of an electrode can be accomplished using alternating or direct current. Any suitable voltage may be used. For example, an electrode may be activated using a voltage which is greater than about 150 V, or greater than about 200 V, or greater than about 250 V, or from about 275 V to about 375 V, or about 300 V. Where alternating current is used, any suitable frequency may be employed. For example, an electrode may be activated using alternating current having a frequency from about 1 Hz to about 100 Hz, or from about 10 Hz to about 60 Hz, or from about 20 Hz to about 40 Hz, or about 30 Hz.

"Bead," with respect to beads on a droplet actuator, means any bead or particle that is capable of interacting with a droplet on or in proximity with a droplet actuator. Beads may be any of a wide variety of shapes, such as spherical, generally spherical, egg shaped, disc shaped, cubical, amorphous and other three dimensional shapes. The bead may, for example, be capable of being subjected to a droplet operation in a droplet on a droplet actuator or otherwise configured with respect to a droplet actuator in a manner which permits a droplet on the droplet actuator to be brought into contact with the bead on the droplet actuator and/or off the droplet actuator. Beads may be provided in a droplet, in a droplet operations gap, or on a droplet operations surface. Beads may be provided in a reservoir that is external to a droplet operations gap or situated apart from a droplet operations surface, and the reservoir may be associated with a fluid path that permits a droplet including the beads to be brought into a droplet operations gap or into contact with a droplet operations surface. Beads may be manufactured using a wide variety of materials, including for example, resins, and polymers. The beads may be any suitable size, including for example, microbeads, microparticles, nanobeads and nanoparticles. In some cases, beads are magnetically responsive; in other cases beads are not significantly magnetically responsive. For magnetically responsive beads, the magnetically responsive material may constitute substantially all of a bead, a portion of a bead, or only one component of a bead. The remainder of the bead may include, among other things, polymeric material, coatings, and moieties which permit attachment of an assay reagent. Examples of suitable beads include flow cytometry microbeads, polystyrene microparticles and nanoparticles, functionalized polystyrene microparticles and nanoparticles, coated polystyrene microparticles and nanoparticles, silica microbeads, fluorescent microspheres and nanospheres, functionalized fluorescent microspheres and nanospheres, coated fluorescent microspheres and nanospheres, color dyed microparticles and nanoparticles, magnetic microparticles and nanoparticles, superparamagnetic microparticles and nanoparticles (e.g., DYNABEADS® particles, available from Invitrogen Group, Carlsbad, Calif.), fluorescent microparticles and nanoparticles, coated magnetic microparticles and nanoparticles, ferromagnetic microparticles and nanoparticles, coated ferromagnetic microparticles and nanoparticles, and those described in U.S. Patent Publication Nos. 20050260686, entitled "Multiplex flow assays preferably with magnetic particles as solid phase," published on Nov. 24, 2005; 20030132538, entitled "Encapsulation of discrete quanta of fluorescent particles," published on Jul. 17, 2003; 20050118574, entitled "Multiplexed Analysis of Clinical Specimens Apparatus and Method," published on Jun. 2, 2005; 20050277197. Entitled "Microparticles with Multiple Fluorescent Signals and Methods of Using Same," published on Dec. 15, 2005; 20060159962, entitled "Magnetic Microspheres for use in Fluorescence-based Applications," published on Jul. 20, 2006; the entire disclosures of which are incorporated herein by reference for their teaching concerning beads and magnetically responsive materials and beads. Beads may be pre-coupled with a biomolecule or other substance that is able to bind to and form a complex with a biomolecule. Beads may be pre-coupled with an antibody, protein or antigen, DNA/RNA probe or any other molecule with an affinity for a desired target. Examples of droplet actuator techniques for immobilizing magnetically responsive beads and/or non-magnetically responsive beads and/or conducting droplet operations protocols using beads are described in U.S. patent application Ser. No. 11/639,566, entitled "Droplet-Based Particle Sorting," filed on Dec. 15, 2006; U.S. Patent Application No. 61/039,183, entitled "Multiplexing Bead Detection in a Single Droplet," filed on Mar. 25, 2008; U.S. Patent Application No. 61/047,789, entitled "Droplet Actuator Devices and Droplet Operations Using Beads," filed on Apr. 25, 2008; U.S. Patent Application No. 61/086,183, entitled "Droplet Actuator Devices and Methods for Manipulating Beads," filed on Aug. 5, 2008; International Patent Application No. PCT/US2008/053545, entitled "Droplet Actuator Devices and Methods Employing Magnetic Beads," filed on Feb. 11, 2008; International Patent Application No. PCT/US2008/058018, entitled "Bead-based Multiplexed Analytical Methods and Instrumentation," filed on Mar. 24, 2008; International Patent Application No. PCT/US2008/058047, "Bead Sorting on a Droplet Actuator," filed on Mar. 23, 2008; and International Patent Application No. PCT/US2006/047486, entitled "Droplet-based Biochemistry," filed on Dec. 11, 2006; the entire disclosures of which are incorporated herein by reference. Bead characteristics may be employed in the multiplexing aspects of the invention. Examples of beads having characteristics suitable for multiplexing, as well as methods of detecting and analyzing signals emitted from such beads, may be found in U.S. Patent Publication No. 20080305481, entitled "Systems and Methods for Multiplex Analysis of PCR in Real Time," published on Dec. 11, 2008; U.S. Patent Publication No. 20080151240, "Methods and Systems for Dynamic Range Expansion," published on Jun. 26, 2008; U.S. Patent Publication No. 20070207513, entitled "Methods, Products, and Kits for Identifying an Analyte in a Sample," published on Sep. 6, 2007; U.S. Patent Publication No. 20070064990, entitled "Methods and Systems for Image Data Processing," published on Mar. 22, 2007; U.S. Patent Publication No. 20060159962, entitled "Magnetic Microspheres for use in Fluorescence-based Applications," published on Jul. 20, 2006; U.S. Patent Publication No. 20050277197, entitled "Microparticles with Multiple Fluorescent Signals and Methods of Using Same," published on Dec. 15, 2005; and U.S. Patent Publication No. 20050118574, entitled "Multiplexed Analysis of Clinical Specimens Apparatus and Method," published on Jun. 2, 2005.

"Droplet" means a volume of liquid on a droplet actuator. Typically, a droplet is at least partially bounded by a filler fluid. For example, a droplet may be completely surrounded by a filler fluid or may be bounded by filler fluid and one or more surfaces of the droplet actuator. As another example, a droplet may be bounded by filler fluid, one or more surfaces of the droplet actuator, and/or the atmosphere. As yet another example, a droplet may be bounded by filler fluid and the atmosphere. Droplets may, for example, be aqueous or non-aqueous or may be mixtures or emulsions including aqueous and non-aqueous components. Droplets may take a wide variety of shapes; nonlimiting examples include generally disc shaped, slug shaped, truncated sphere, ellipsoid, spherical, partially compressed sphere, hemispherical, ovoid, cylindrical, combinations of such shapes, and various shapes formed during droplet operations, such as merging or splitting or formed as a result of contact of such shapes with one or more surfaces of a droplet actuator. For examples of droplet fluids that may be subjected to droplet operations using the approach of the invention, see International Patent Application No. PCT/US 06/47486, entitled, "Droplet-Based Biochemistry," filed on Dec. 11, 2006. In various embodiments, a droplet may include a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, liquids containing single or multiple cells, liquids containing organelles, fluidized tissues, fluidized organisms, liquids containing multi-celled organisms, biological swabs and biological washes. Moreover, a droplet may include a reagent, such as water, deionized water, saline solutions, acidic solutions, basic solutions, detergent solutions and/or buffers. Other examples of droplet contents include reagents, such as a reagent for a biochemical protocol, such as a nucleic acid amplification protocol, an affinity-based assay protocol, an enzymatic assay protocol, a sequencing protocol, and/or a protocol for analyses of biological fluids.

"Droplet Actuator" means a device for manipulating droplets. For examples of droplet actuators, see Pamula et al., U.S. Pat. No. 6,911,132, entitled "Apparatus for Manipulating Droplets by Electrowetting-Based Techniques," issued on Jun. 28, 2005; Pamula et al., U.S. patent application Ser. No. 11/343,284, entitled "Apparatuses and Methods for Manipulating Droplets on a Printed Circuit Board," filed on filed on Jan. 30, 2006; Pollack et al., International Patent Application No. PCT/US2006/047486, entitled "Droplet-Based Biochemistry," filed on Dec. 11, 2006; Shenderov, U.S. Pat. No. 6,773,566, entitled "Electrostatic Actuators for Microfluidics and Methods for Using Same," issued on Aug. 10, 2004 and U.S. Pat. No. 6,565,727, entitled "Actuators for Microfluidics Without Moving Parts," issued on Jan. 24, 2000; Kim and/or Shah et al., U.S. patent application Ser. No. 10/343,261, entitled "Electrowetting-driven Micropumping," filed on Jan. 27, 2003, Ser. No. 11/275,668, entitled "Method and Apparatus for Promoting the Complete Transfer of Liquid Drops from a Nozzle," filed on Jan. 23, 2006, Ser. No. 11/460,188, entitled "Small Object Moving on Printed Circuit Board," filed on Jan. 23, 2006, Ser. No. 12/465,935, entitled "Method for Using Magnetic Particles in Droplet Microfluidics," filed on May 14, 2009, and Ser. No. 12/513,157, entitled "Method and Apparatus for Real-time Feedback Control of Electrical Manipulation of Droplets on Chip," filed on Apr. 30, 2009; Velev, U.S. Pat. No. 7,547,380, entitled "Droplet Transportation Devices and Methods Having a Fluid Surface," issued on Jun. 16, 2009; Sterling et al., U.S. Pat. No. 7,163,612, entitled "Method, Apparatus and Article for Microfluidic Control via Electrowetting, for Chemical, Biochemical and Biological Assays and the Like," issued on Jan. 16, 2007; Becker and Gascoyne et al., U.S. Pat. No. 7,641,779, entitled "Method and Apparatus for Programmable fluidic Processing," issued on Jan. 5, 2010, and U.S. Pat. No. 6,977,033, entitled "Method and Apparatus for Programmable fluidic Processing," issued on Dec. 20, 2005; Decre et al., U.S. Pat. No. 7,328,979, entitled "System for Manipulation of a Body of Fluid," issued on Feb. 12, 2008; Yamakawa et al., U.S. Patent Pub. No. 20060039823, entitled "Chemical Analysis Apparatus," published on Feb. 23, 2006; Wu, International Patent Pub. No. WO/2009/003184, entitled "Digital Microfluidics Based Apparatus for Heat-exchanging Chemical Processes," published on Dec. 31, 2008; Fouillet et al., U.S. Patent Pub.

No. 20090192044, entitled "Electrode Addressing Method," published on Jul. 30, 2009; Fouillet et al., U.S. Pat. No. 7,052,244, entitled "Device for Displacement of Small Liquid Volumes Along a Micro-catenary Line by Electrostatic Forces," issued on May 30, 2006; Marchand et al., U.S. Patent Pub. No. 20080124252, entitled "Droplet Microreactor," published on May 29, 2008; Adachi et al., U.S. Patent Pub. No. 20090321262, entitled "Liquid Transfer Device," published on Dec. 31, 2009; Roux et al., U.S. Patent Pub. No. 20050179746, entitled "Device for Controlling the Displacement of a Drop Between two or Several Solid Substrates," published on Aug. 18, 2005; Dhindsa et al., "Virtual Electrowetting Channels: Electronic Liquid Transport with Continuous Channel Functionality," *Lab Chip*, 10:832-836 (2010); the entire disclosures of which are incorporated herein by reference, along with their priority documents. Certain droplet actuators will include one or more substrates arranged with a gap therebetween and electrodes associated with (e.g., layered on, attached to, and/or embedded in) the one or more substrates and arranged to conduct one or more droplet operations. For example, certain droplet actuators will include a base (or bottom) substrate, droplet operations electrodes associated with the substrate, one or more dielectric layers atop the substrate and/or electrodes, and optionally one or more hydrophobic layers atop the substrate, dielectric layers and/or the electrodes forming a droplet operations surface. A top substrate may also be provided, which is separated from the droplet operations surface by a gap, commonly referred to as a droplet operations gap. Various electrode arrangements on the top and/or bottom substrates are discussed in the above-referenced patents and applications and certain novel electrode arrangements are discussed in the description of the invention. During droplet operations it is preferred that droplets remain in continuous contact or frequent contact with a ground or reference electrode. A ground or reference electrode may be associated with the top substrate facing the gap, the bottom substrate facing the gap, in the gap. Where electrodes are provided on both substrates, electrical contacts for coupling the electrodes to a droplet actuator instrument for controlling or monitoring the electrodes may be associated with one or both plates. In some cases, electrodes on one substrate are electrically coupled to the other substrate so that only one substrate is in contact with the droplet actuator. In one embodiment, a conductive material (e.g., an epoxy, such as MASTER BOND™ Polymer System EP79, available from Master Bond, Inc., Hackensack, N.J.) provides the electrical connection between electrodes on one substrate and electrical paths on the other substrates, e.g., a ground electrode on a top substrate may be coupled to an electrical path on a bottom substrate by such a conductive material. Where multiple substrates are used, a spacer may be provided between the substrates to determine the height of the gap therebetween and define dispensing reservoirs. The spacer height may, for example, be from about 5 µm to about 600 µm, or about 100 µm to about 400 µm, or about 200 µm to about 350 µm, or about 250 µm to about 300 µm, or about 275 µm. The spacer may, for example, be formed of a layer of projections form the top or bottom substrates, and/or a material inserted between the top and bottom substrates. One or more openings may be provided in the one or more substrates for forming a fluid path through which liquid may be delivered into the droplet operations gap. The one or more openings may in some cases be aligned for interaction with one or more electrodes, e.g., aligned such that liquid flowed through the opening will come into sufficient proximity with one or more droplet operations electrodes to permit a droplet operation to be effected by the droplet operations electrodes using the liquid. The base (or bottom) and top substrates may in some cases be formed as one integral component. One or more reference electrodes may be provided on the base (or bottom) and/or top substrates and/or in the gap. Examples of reference electrode arrangements are provided in the above referenced patents and patent applications. In various embodiments, the manipulation of droplets by a droplet actuator may be electrode mediated, e.g., electrowetting mediated or dielectrophoresis mediated or Coulombic force mediated. Examples of other techniques for controlling droplet operations that may be used in the droplet actuators of the invention include using devices that induce hydrodynamic fluidic pressure, such as those that operate on the basis of mechanical principles (e.g. external syringe pumps, pneumatic membrane pumps, vibrating membrane pumps, vacuum devices, centrifugal forces, piezoelectric/ultrasonic pumps and acoustic forces); electrical or magnetic principles (e.g. electroosmotic flow, electrokinetic pumps, ferrofluidic plugs, electrohydrodynamic pumps, attraction or repulsion using magnetic forces and magnetohydrodynamic pumps); thermodynamic principles (e.g. gas bubble generation/phase-change-induced volume expansion); other kinds of surface-wetting principles (e.g. electrowetting, and optoelectrowetting, as well as chemically, thermally, structurally and radioactively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential. In certain embodiments, combinations of two or more of the foregoing techniques may be employed to conduct a droplet operation in a droplet actuator of the invention. Similarly, one or more of the foregoing may be used to deliver liquid into a droplet operations gap, e.g., from a reservoir in another device or from an external reservoir of the droplet actuator (e.g., a reservoir associated with a droplet actuator substrate and a fluid path from the reservoir into the droplet operations gap). Droplet operations surfaces of certain droplet actuators of the invention may be made from hydrophobic materials or may be coated or treated to make them hydrophobic. For example, in some cases some portion or all of the droplet operations surfaces may be derivatized with low surface-energy materials or chemistries, e.g., by deposition or using in situ synthesis using compounds such as poly- or per-fluorinated compounds in solution or polymerizable monomers. Examples include TEFLON® AF (available from DuPont, Wilmington, Del.), members of the cytop family of materials, coatings in the FLUOROPEL® family of hydrophobic and superhydrophobic coatings (available from Cytonix Corporation, Beltsville, Md.), silane coatings, fluorosilane coatings, hydrophobic phosphonate derivatives (e.g., those sold by Aculon, Inc), and NOVEC™ electronic coatings (available from 3M Company, St. Paul, Minn.), and other fluorinated monomers for plasma-enhanced chemical vapor deposition (PECVD). In some cases, the droplet operations surface may include a hydrophobic coating having a thickness ranging from about 10 nm to about 1,000 nm. Moreover, in some embodiments, the top substrate of the droplet actuator includes an electrically conducting organic polymer, which is then coated with a hydrophobic coating or otherwise treated to make the droplet operations surface hydrophobic. For example, the electrically conducting organic polymer that is deposited onto a plastic substrate may be poly(3,4-ethylenedioxythiophene)poly(styrene-sulfonate) (PEDOT:PSS). Other examples of electrically conducting organic polymers and alternative conductive layers are described in Pollack et al., International Patent Application No. PCT/US2010/040705, entitled "Droplet Actuator Devices and Methods," the entire disclosure of which is incorporated herein by reference. One or both substrates may be fabricated using a printed circuit board (PCB), glass, indium tin oxide (ITO)-coated glass, and/or semiconductor materials as the substrate. When the substrate is ITO-coated glass, the ITO coating is preferably a thickness in the range of about 20 to about 200 nm, preferably about 50 to about 150 nm, or about 75 to about 125 nm, or about 100 nm. In some cases, the top and/or bottom substrate includes a PCB substrate that is coated with a dielectric, such as a polyimide dielectric, which may in some cases also be coated or otherwise treated to make the droplet operations surface hydrophobic. When the substrate includes a PCB, the following materials are examples of suitable materials: MITSUI™ BN-300 (available from MITSUI Chemicals America, Inc., San Jose Calif.); ARLON™ 11N (available from Arlon, Inc, Santa Ana, Calif.).; NELCO® N4000-6 and N5000-30/32 (available from Park Electrochemical Corp., Melville, N.Y.); ISOLA™ FR406 (available from Isola Group, Chandler, Ariz.), especially IS620; fluoropolymer family (suitable for fluorescence detection since it has low background fluorescence); polyimide family; polyester; polyethylene naphthalate; polycarbonate; polyetheretherketone; liquid crystal polymer; cyclo-olefin copolymer (COC); cyclo-olefin polymer (COP); aramid; THERMOUNT® nonwoven aramid reinforcement (available from DuPont, Wilmington, Del.); NOMEX® brand fiber (available from DuPont, Wilmington, Del.); and paper. Various materials are also suitable for use as the dielectric component of the substrate. Examples include: vapor deposited dielectric, such as PARYLENE™ C (especially on glass) and PARYLENE™ N (available from Parylene Coating Services, Inc., Katy, Tex.); TEFLON® AF coatings; cytop; soldermasks, such as liquid photoimageable soldermasks (e.g., on PCB) like TAIYO™ PSR4000 series, TAIYO™ PSR and AUS series (available from Taiyo America, Inc. Carson City, Nev.) (good thermal characteristics for applications involving thermal control), and PROBIMER™ 8165 (good thermal characteristics for applications involving thermal control (available from Huntsman Advanced Materials Americas Inc., Los Angeles, Calif.); dry film soldermask, such as those in the VACREL® dry film soldermask line (available from DuPont, Wilmington, Del.); film dielectrics, such as polyimide film (e.g., KAPTON® polyimide film, available from DuPont, Wilmington, Del.), polyethylene, and fluoropolymers (e.g., FEP), polytetrafluoroethylene; polyester; polyethylene naphthalate; cyclo-olefin copolymer (COC); cyclo-olefin polymer (COP); any other PCB substrate material listed above; black matrix resin; and polypropylene. Droplet transport voltage and frequency may be selected for performance with reagents used in specific assay protocols. Design parameters may be varied, e.g., number and placement of on-actuator reservoirs, number of independent electrode connections, size (volume) of different reservoirs, placement of magnets/bead washing zones, electrode size, inter-electrode pitch, and gap height (between top and bottom substrates) may be varied for use with specific reagents, protocols, droplet volumes, etc. In some cases, a substrate of the invention may derivatized with low surface-energy materials or chemistries, e.g., using deposition or in situ synthesis using poly- or per-fluorinated compounds in solution or polymerizable monomers. Examples include TEFLON® AF coatings and FLUOROPEL® coatings for dip or spray coating, and other fluorinated monomers for plasma-enhanced chemical vapor deposition (PECVD). Additionally, in some cases, some portion or all of the droplet operations surface may be coated with a substance for reducing background noise, such as background fluorescence from a PCB substrate. For example, the noise-reducing coating may include a black matrix resin, such as the black matrix resins available from Toray industries, Inc., Japan. Electrodes of a droplet actuator are typically controlled by a controller or a processor, which is itself provided as part of a system, which may include processing functions as well as data and software storage and input and output capabilities. Reagents may be provided on the droplet actuator in the droplet operations gap or in a reservoir fluidly coupled to the droplet operations gap. The reagents may be in liquid form, e.g., droplets, or they may be provided in a reconstitutable form in the droplet operations gap or in a reservoir fluidly coupled to the droplet operations gap. Reconstitutable reagents may typically be combined with liquids for reconstitution. An example of reconstitutable reagents suitable for use with the invention includes those described in Meathrel, et al., U.S. Pat. No. 7,727,466, entitled "Disintegratable films for diagnostic devices," granted on Jun. 1, 2010.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to volume of the resulting droplets (i.e., the volume of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles. For examples of droplet operations, see the patents and patent applications cited above under the definition of "droplet actuator." Impedance or capacitance sensing or imaging techniques may sometimes be used to determine or confirm the outcome of a droplet operation. Examples of such techniques are described in Sturmer et al., International Patent Pub. No. WO/2008/101194, entitled "Capacitance Detection in a Droplet Actuator," published on Aug. 21, 2008, the entire disclosure of which is incorporated herein by reference. Generally speaking, the sensing or imaging techniques may be used to confirm the presence or absence of a droplet at a specific electrode. For example, the presence of a dispensed droplet at the destination electrode following a droplet dispensing operation confirms that the droplet dispensing operation was effective. Similarly, the presence of a droplet at a detection spot at an appropriate step in an assay protocol may confirm that a previous set of droplet operations has successfully produced a droplet for detection. Droplet transport time can be quite fast. For example, in various embodiments, transport of a droplet from one electrode to the next may exceed about 1 sec, or about 0.1 sec, or about 0.01 sec, or about 0.001 sec. In one embodiment, the electrode is operated in AC mode but is switched to DC mode for imaging. It is helpful for conducting droplet operations for the footprint area of droplet to be similar to electrowetting area; in other words, 1x-, 2x- 3x-droplets are usefully controlled operated using 1, 2, and 3 electrodes, respectively. If the droplet footprint is greater than the number of electrodes available for conducting a droplet operation at a given time, the difference between the droplet size and the number of electrodes should typically not be greater than 1; in other words, a 2x droplet is usefully controlled using 1 electrode and a 3x droplet is usefully controlled using 2 electrodes. When droplets include beads, it is useful for droplet size to be equal to the number of electrodes controlling the droplet, e.g., transporting the droplet.

"Filler fluid" means a fluid associated with a droplet operations substrate of a droplet actuator, which fluid is sufficiently immiscible with a droplet phase to render the droplet phase subject to electrode-mediated droplet operations. For example, the gap of a droplet actuator is typically filled with a filler fluid. The filler fluid may, for example, be a low-viscosity oil, such as silicone oil or hexadecane filler fluid. The filler fluid may fill the entire gap of the droplet actuator or may coat one or more surfaces of the droplet actuator. Filler fluids may be conductive or non-conductive. Filler fluids may, for example, be doped with surfactants or other additives. For example, additives may be selected to improve droplet operations and/or reduce loss of reagent or target substances from droplets, formation of microdroplets, cross contamination between droplets, contamination of droplet actuator surfaces, degradation of droplet actuator materials, etc. Composition of the filler fluid, including surfactant doping, may be selected for performance with reagents used in the specific assay protocols and effective interaction or non-interaction with droplet actuator materials. Examples of filler fluids and filler fluid formulations suitable for use with the invention are provided in Srinivasan et al, International Patent Pub. Nos. WO/2010/027894, entitled "Droplet Actuators, Modified Fluids and Methods," published on Mar. 11, 2010, and WO/2009/021173, entitled "Use of Additives for Enhancing Droplet Operations," published on Feb. 12, 2009; Sista et al., International Patent Pub. No. WO/2008/098236, entitled "Droplet Actuator Devices and Methods Employing Magnetic Beads," published on Aug. 14, 2008; and Monroe et al., U.S. Patent Publication No. 20080283414, entitled "Electrowetting Devices," filed on May 17, 2007; the entire disclosures of which are incorporated herein by reference, as well as the other patents and patent applications cited herein.

"Immobilize" with respect to magnetically responsive beads, means that the beads are substantially restrained in position in a droplet or in filler fluid on a droplet actuator. For example, in one embodiment, immobilized beads are sufficiently restrained in position in a droplet to permit execution of a droplet splitting operation, yielding one droplet with substantially all of the beads and one droplet substantially lacking in the beads.

"Magnetically responsive" means responsive to a magnetic field. "Magnetically responsive beads" include or are composed of magnetically responsive materials. Examples of magnetically responsive materials include paramagnetic materials, ferromagnetic materials, ferrimagnetic materials, and metamagnetic materials. Examples of suitable paramagnetic materials include iron, nickel, and cobalt, as well as metal oxides, such as $Fe_3O_4$, $BaFe_{12}O_{19}$, $CoO$, $NiO$, $Mn_2O_3$, $Cr_2O_3$, and $CoMnP$.

"Reservoir" means an enclosure or partial enclosure configured for holding, storing, or supplying liquid. A droplet actuator system of the invention may include on-cartridge reservoirs and/or off-cartridge reservoirs. On-cartridge reservoirs may be (1) on-actuator reservoirs, which are reservoirs in the droplet operations gap or on the droplet operations surface; (2) off-actuator reservoirs, which are reservoirs on the droplet actuator cartridge, but outside the droplet operations gap, and not in contact with the droplet operations surface; or (3) hybrid reservoirs which have on-actuator regions and off-actuator regions. An example of an off-actuator reservoir is a reservoir in the top substrate. An off-actuator reservoir is typically in fluid communication with an opening or fluid path arranged for flowing liquid from the off-actuator reservoir into the droplet operations gap, such as into an on-actuator reservoir. An off-cartridge reservoir may be a reservoir that is not part of the droplet actuator cartridge at all, but which flows liquid to some portion of the droplet actuator cartridge. For example, an off-cartridge reservoir may be part of a system or docking station to which the droplet actuator cartridge is coupled during operation. Similarly, an off-cartridge reservoir may be a reagent storage container or syringe which is used to force fluid into an on-cartridge reservoir or into a droplet operations gap. A system using an off-cartridge reservoir will typically include a fluid passage means whereby liquid may be transferred from the off-cartridge reservoir into an on-cartridge reservoir or into a droplet operations gap.

"Transporting into the magnetic field of a magnet," "transporting towards a magnet," and the like, as used herein to refer to droplets and/or magnetically responsive beads within droplets, is intended to refer to transporting into a region of a magnetic field capable of substantially attracting magnetically responsive beads in the droplet. Similarly, "transporting away from a magnet or magnetic field," "transporting out of the magnetic field of a magnet," and the like, as used herein to refer to droplets and/or magnetically responsive beads within droplets, is intended to refer to transporting away from a region of a magnetic field capable of substantially attracting magnetically responsive beads in the droplet, whether or not the droplet or magnetically responsive beads is completely removed from the magnetic field. It will be appreciated that in any of such cases described herein, the droplet may be transported towards or away from the desired region of the magnetic field, and/or the desired region of the magnetic field may be moved towards or away from the droplet. Reference to an electrode, a droplet, or magnetically responsive beads being "within" or "in" a magnetic field, or the like, is intended to describe a situation in which the electrode is situated in a manner which permits the electrode to transport a droplet into and/or away from a desired region of a magnetic field, or the droplet or magnetically responsive beads is/are situated in a desired region of the magnetic field, in each case where the magnetic field in the desired region is capable of substantially attracting any magnetically responsive beads in the droplet. Similarly, reference to an electrode, a droplet, or magnetically responsive beads being "outside of" or "away from" a magnetic field, and the like, is intended to describe a situation in which the electrode is situated in a manner which permits the electrode to transport a droplet away from a certain region of a magnetic field, or the droplet or magnetically responsive beads is/are situated away from a certain region of the magnetic field, in each case where the magnetic field in such region is not capable of substantially attracting any magnetically responsive beads in the droplet or in which any remaining attraction does not eliminate the effectiveness of droplet operations conducted in the region. In various aspects of the invention, a system, a droplet actuator, or another component of a system may include a magnet, such as one or more permanent magnets (e.g., a single cylindrical or bar magnet or an array of such magnets, such as a Halbach array) or an electromagnet or array of electromagnets, to form a magnetic field for interacting with magnetically responsive beads or other components on chip. Such interactions may, for example, include substantially immobilizing or restraining movement or flow of magnetically responsive beads during storage or in a droplet during a droplet operation or pulling magnetically responsive beads out of a droplet.

"Washing" with respect to washing a bead means reducing the amount and/or concentration of one or more substances in contact with the bead or exposed to the bead from a droplet in contact with the bead. The reduction in the amount and/or concentration of the substance may be partial, substantially complete, or even complete. The substance may be any of a wide variety of substances; examples include target substances for further analysis, and unwanted substances, such as components of a sample, contaminants, and/or excess reagent. In some embodiments, a washing operation begins with a starting droplet in contact with a magnetically responsive bead, where the droplet includes an initial amount and initial concentration of a substance. The washing operation may proceed using a variety of droplet operations. The washing operation may yield a droplet including the magnetically responsive bead, where the droplet has a total amount and/or concentration of the substance which is less than the initial amount and/or concentration of the substance. Examples of suitable washing techniques are described in Pamula et al., U.S. Pat. No. 7,439,014, entitled "Droplet-Based Surface Modification and Washing," granted on Oct. 21, 2008, the entire disclosure of which is incorporated herein by reference.

The terms "top," "bottom," "over," "under," and "on" are used throughout the description with reference to the relative positions of components of the droplet actuator, such as relative positions of top and bottom substrates of the droplet actuator. It will be appreciated that the droplet actuator is functional regardless of its orientation in space.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct one or more droplet operations on the droplet, the droplet is arranged on the droplet actuator in a manner which facilitates sensing of a property of or a signal from the droplet, and/or the droplet has been subjected to a droplet operation on the droplet actuator.

5 BRIEF DESCRIPTION OF THE DRAWINGS

6 DESCRIPTION

Figure 1:
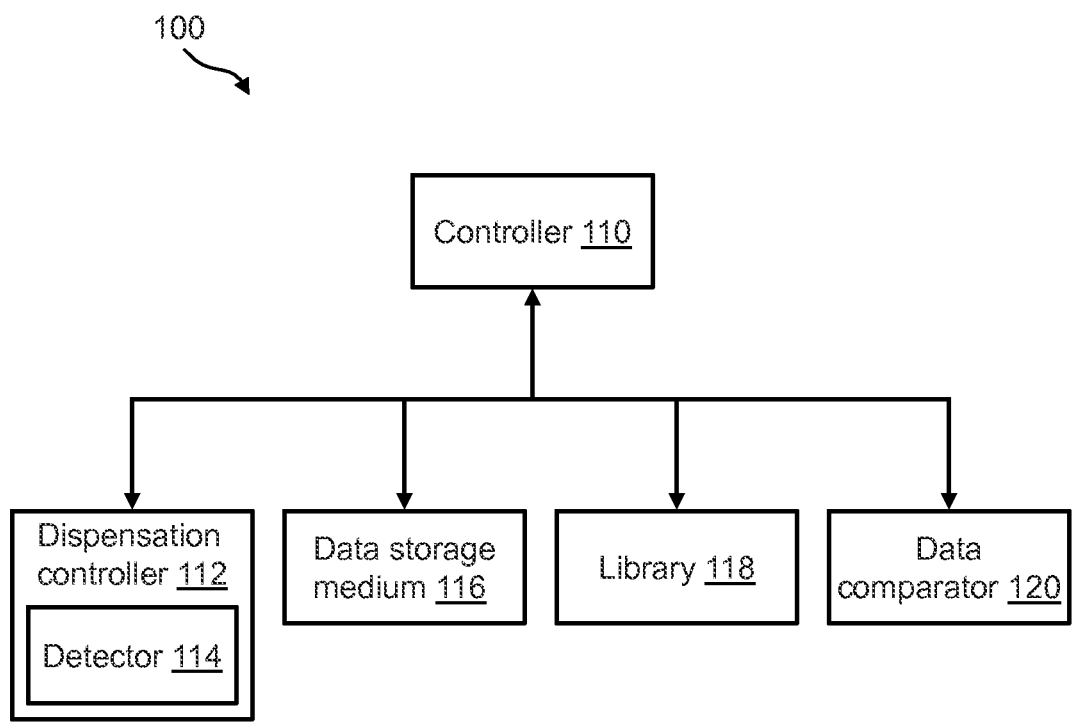
FIG. 1 illustrates a functional block diagram of an example of a sequencing system for hybrid pyrosequencing.

The invention provides systems and methods for varying the dispensation order of nucleotides in a pyrosequencing reaction depending on the specific sample being analyzed. In one embodiment, the methods of the invention use a guided approach to pyrosequencing (i.e., hybrid pyrosequencing) in which a de novo sequence is compared to a database(s) of possible results and the next nucleotide to be dispensed is selected based the most probable base for that position. The database of possible results may include predetermined possible candidate sequences and non-sequence parameters, such as organism type and incidence of infection, diagnostic symptoms, and/or sample source. In another embodiment, the methods of the invention use a combination of pyrosequencing protocols, e.g., de novo sequencing, directed pyrosequencing, and hybrid pyrosequencing, to rapidly and efficiently determine target nucleic acid sequences in a sample being analyzed.

The systems and methods of the invention may be used to rapidly and efficiently identify one or more organisms in a sample. The sample may, for example, be a biological sample or an environmental sample. In one example, the systems and methods of the invention may be used to identify and type clinically relevant microorganisms such as bacteria, viruses and fungi. In another example, the systems and methods of the invention may be used to rule out known organisms and determine the sequence of an unknown organism(s) in a sample.

The methods of the invention are applicable to a variety of pyrosequencing platforms. In one embodiment, the system and methods of the invention are used in droplet-based pyrosequencing on a droplet actuator.

6.1 Hybrid Pyrosequencing

The systems and methods of the invention provide a guided approach to pyrosequencing (i.e., hybrid pyrosequencing). In various embodiments, a de novo nucleic acid sequence is compared to a library of possible results and the next nucleotide to be dispensed is selected based on the comparison of the de novo sequence and the library of possible results. In one embodiment, at least the first nucleotide to be dispensed is selected based on a query of a database(s) of non-sequence parameters (e.g., incidence of infection, diagnostic symptoms, sample source) and subsequent dispensations determined based on a comparison of the de novo sequence and the library of possible results (e.g., candidate sequences).

Pyrosequencing is a sequencing-by-synthesis method in which a primed DNA template strand is sequentially exposed to one of four deoxynucleotide triphosphates (dNTPs) in the presence of DNA polymerase. If the added nucleotide is complementary to the next unpaired base, then it is incorporated by the polymerase and inorganic pyrophosphate (PPi) is released. Real-time detection of PPi occurs through an enzymatic cascade in which PPi is converted by a second enzyme, sulfurylase, to ATP which provides energy for a third enzyme, luciferase, to oxidize luciferin and generate a light signal. The amount of light generated is proportional to the number of adjacent unpaired bases complementary to the added nucleotide. In some pyrosequencing protocols, a fourth enzyme, apyrase, is used to degrade the excess dNTP and ATPs prior to the next reaction cycle, i.e., another nucleotide addition. Nucleotide incorporation proceeds sequentially along each template as each nucleotide is made available. In one example, each nucleotide may be made available in a preselected or programmed order. In another example, each nucleotide may be made available in a dynamic order, i.e., a continuously changing order.

The methods of hybrid pyrosequencing of the invention include detecting a measurable signal produced by a reaction when a nucleotide is incorporated into a de novo nucleic acid sequence, registering and storing the detected nucleic acid sequence, comparing the detected sequence to a retrievable (searchable) library of possible results, and adapting the order of following nucleotide dispensations in response to the comparison of the detected and registered sequence and the library of possible results. A library of possible results may include, but is not limited to, a database of a plurality of candidate sequences that is likely to include the detected and registered nucleic acid sequence; a database of incidence of infection and organism type; and a database of diagnostic symptoms and organism type. In various embodiments, the methods of the invention uses a combination of selection (separation) algorithms to query a library of possible results and adapt the order of nucleotide dispensation in response to a measurable signal produced by a reaction when a nucleotide is incorporated into a de novo sequence. Each time a nucleotide is dispensed, the nucleotide is either incorporated or not. Based on the returned information signal, certain candidate sequences in the library that do not match the de novo sequence can be eliminated as possible results. As nucleotides are dispensed, the number of candidates is successively decreased until only one or a few alternatives remain.

FIG. 1 illustrates a functional block diagram of an example of a sequencing system 100 for hybrid pyrosequencing. Sequencing system 100 may include a controller 110, which controls the overall operation of the system. Controller 110 may, for example, be a computerized user terminal, such as a personal computer. Sequencing system 100 may also include a dispensation controller 112. Dispensation controller 112 is the principal signal analysis and control means of sequencing system 100. A detector 114 is associated with dispensation controller 112. Detector 114 is used to determine whether a dispensed nucleotide is incorporated in the nucleotide sequence of the molecule. Sequencing system 100 may also include data storage medium 116 and a library 118. Data storage medium 116 may, for example, be a state of the art non-volatile or other persistent memory. Data storage medium 116 may be used to register and store detected nucleic acid sequence. In one example, library 118 may include, but is not limited to, a collection of a plurality of possible sequences of the detected and registered nucleic acid sequence; a collection of incidence of infection and organism type; and a collection of diagnostic symptoms.

Sequencing system 100 may also include a data comparator 120. In one example, data comparator 120 may be an integral part of dispensation controller 112. In another example, data comparator 120 may be provided separate from dispensation controller 112. Data (e.g., registered and detected sequences) from data storage medium 116 and the contents of library 118 may be compared using data comparator 120. For example, data comparator 120 is used to retrieve the detected registered nucleic acid sequence stored in data storage medium 116 and then compares this information with possible results in library 118. Based on the returned information signal, certain candidate sequences or allele combinations in the library that do not match the registered and detected sequence (de novo sequence) can be eliminated because they are no longer possible sequences and, thus, can be neglected. Dispensation controller 112 is used to process a response signal and adapt the order of following dispensations in response to the comparison of the detected and registered sequence and the library of possible results. As nucleotides are dispensed, the amount of candidates is successively decreased.

Figure 2:
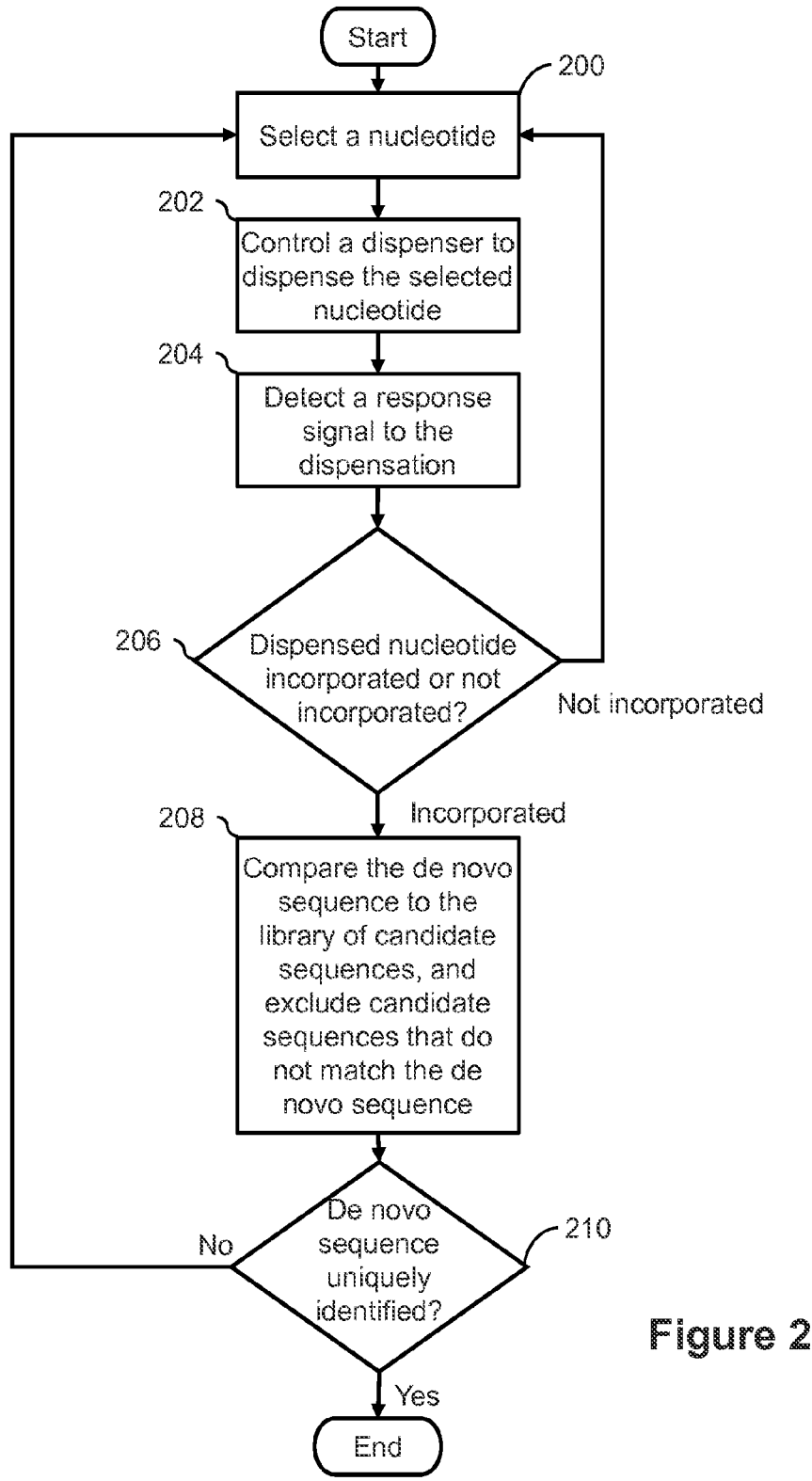
FIG. 2 illustrates a flow diagram of an example method for identifying a nucleic acid sequence in a sample by hybrid pyrosequencing.

FIG. 2 illustrates a flow diagram of an example method for identifying a nucleic acid sequence in a sample by hybrid pyrosequencing. The method of FIG. 2 is described as being implemented by the sequencing system 100 shown in FIG. 1; although the method may otherwise be implemented by any suitable system.

Referring to FIG. 2, the method includes selecting a nucleotide to be dispensed to a sample comprising a primed DNA template and reagents sufficient for sequencing-by-synthesis of a de novo nucleic acid sequence to be identified (step 200). The selection may be based on a query of a database of non-sequence parameters and/or a comparison of the de novo sequence to a library of candidate sequences. As an example, controller 110 may be used for selection of a nucleotide to be dispensed. As another example, dispensation controller 112, alone or in combination with controller 110, may be used for selection of a nucleotide to be dispensed.

The method of FIG. 2 includes controlling a dispenser to dispense the selected nucleotide to the sample (step 202). Continuing the aforementioned example, dispensation controller 112 may control suitable dispenser to dispense the selected nucleotide. Controller 110 may suitably operate together with dispensation controller 112 for controlling the dispenser.

The method of FIG. 2 includes detecting a response signal to the dispensation (step 204). Continuing the aforementioned example, detector 114 may detect a response to the dispensation of the selected nucleotide. Further, detector 114 may transmit a response signal representative of the response to dispensation controller 112.

The method of FIG. 2 includes determining whether the dispensed nucleotide was incorporated or not incorporated (step 206). Continuing the aforementioned example, dispensation controller 112 may determine whether the response signal is incorporated or not incorporated. For example, dispensation controller 112 may analyze the signal to determine whether the nucleotide is incorporated or not.

In response to determining that the dispensed nucleotide is not incorporated, the method of FIG. 2 may return to step 200 for repeating steps 200-206. The steps may be repeated until it is determined that a nucleotide selected at step 200 has been incorporated. In response to determining that the dispensed is incorporated, the method may proceed to step 208.

At step 208, the method of FIG. 2 includes comparing the de novo sequence to the library of candidate sequences. Step 208 may also include excluding candidate sequences that do not match the de novo sequence. Continuing the aforementioned example, data comparator 120 may compare the de novo sequence to possible results stored in library 118. Candidate sequences in library 118 that do not match the registered and detected sequence (de novo sequence) can be eliminated or excluded.

The method of FIG. 2 includes determining whether the de novo sequence is uniquely identified (step 210). In response to determining that the de novo sequence has not been uniquely identified, the method may return to step 200 for repeating steps 200-210. The method may end in response to determining that the de novo sequence has been uniquely identified.

Figure 3:
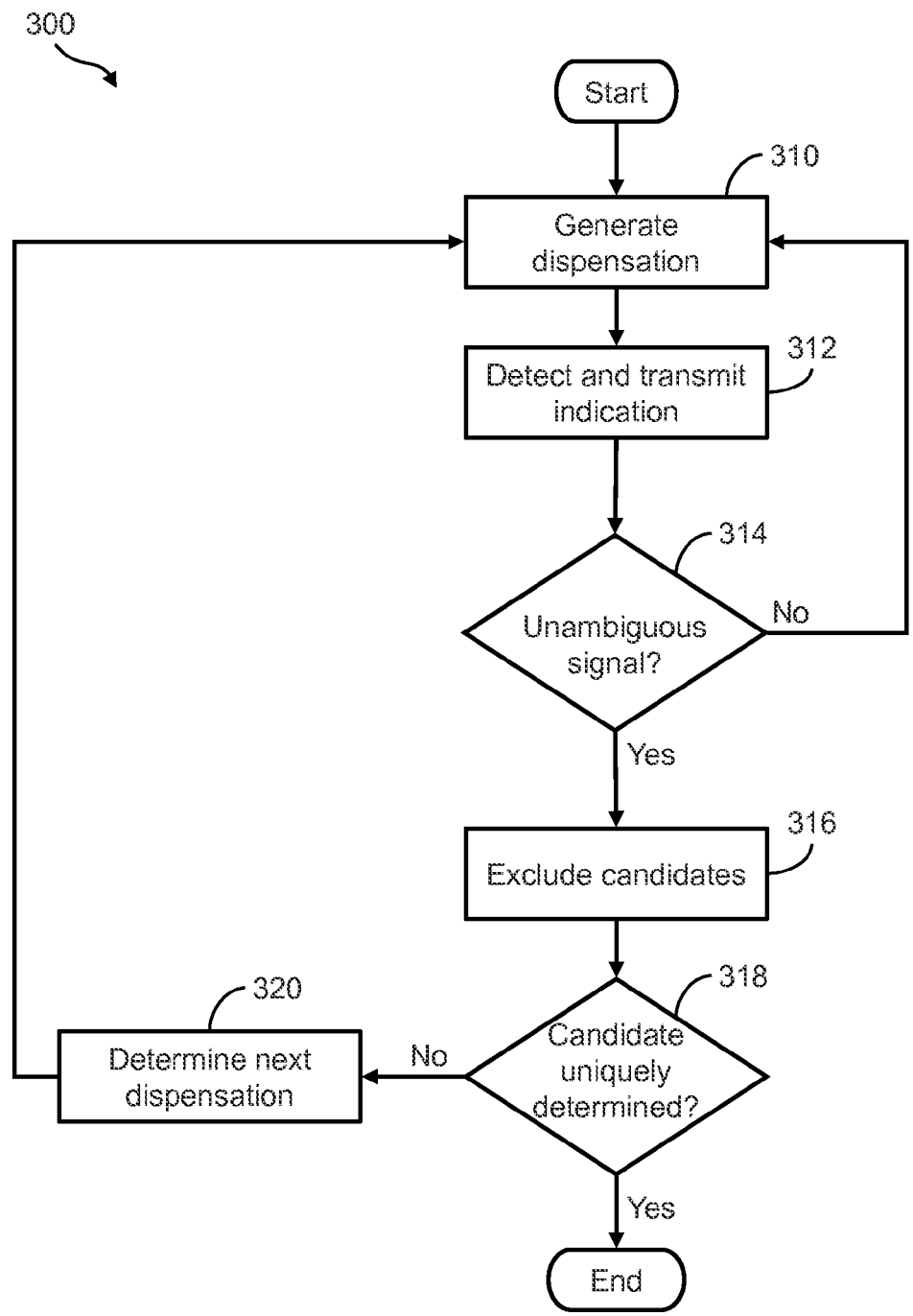
FIG. 3 illustrates a flow diagram of an example of a method of hybrid pyrosequencing using the sequencing system of FIG. 1.

FIG. 3 illustrates a flow diagram of an example of a method 300 of hybrid pyrosequencing using sequencing system 100 of FIG. 1. In this example, selection of at least a first nucleotide to be dispensed is based in part on non-sequence parameters (e.g., incidence of infection and/or diagnostic symptoms) and in part on frequency of a nucleotide in a database of possible candidate sequences. Method 300 may include, but is not limited to, the following steps.

At step 310, the pyrosequencing reaction starts on operator command and a nucleotide is dispensed. Selection of a nucleotide to be dispensed may, for example, be based in part on non-sequence parameters (e.g., incidence of infection and/or diagnostic symptoms) and/or in part on frequency of a nucleotide in a database of possible candidate sequences. In one example, at least the first nucleotide to be dispensed is selected based on a query of a database(s) of non-sequence parameters (e.g., incidence of infection, diagnostic symptoms) and subsequent dispensations determined based on a comparison of the de novo sequence and the library of possible results (e.g., candidate sequences).

At step 312, a signal is detected by detector 114 and transmitted as a response signal to dispensation controller 112.

At decision step 314, dispensation controller 112 determines whether the response signal is unambiguous. If the response signal is not unambiguous, method 300 may return to step 310 to re-initiate the dispensation sequence. However, if the response signal is unambiguous, the response is interpreted as either a signal (nucleotide is incorporated) or lack of signal (nucleotide was not included). In some instances, signal processing may be required (i.e., measuring the program peak heights of detected signals) for incorporated nucleotides to accurately determine genotype. If the response signal is unambiguous, method 300 may proceed to step 316.

At step 316, exclusion of candidates is made. In this step, the de novo sequence is compared to the library of possible results. For example, data comparator 120 is used to retrieve the de novo sequence that is stored in data storage medium 116 and then compare this information with possible results in library 118. Certain candidate sequences in library 118 that do not match the registered and detected sequence (de novo sequence) can be eliminated because they are no longer possible sequences and, thus, can be neglected. The search space is reduced.

At decision step 318, it is determined whether a candidate has been uniquely determined. If a candidate has not been uniquely determined, method 300 may proceed to step 320 and the next dispensation is determined. However, if a candidate has been uniquely determined, method 300 may end.

At step 320, the next dispensation is determined. In this step, the remaining candidate sequences in the possible results of library 118 are queried and the next nucleotide to be dispensed is selected based on the on the most probable nucleotide for that position. The choice of dispensation is made to decrease the library of candidate sequences as much as possible. Method 300 returns to step 310 and the next nucleotide is dispensed. Method 300 may be repeated until a candidate has been uniquely determined or until the candidate library cannot be further decreased.

Any number of variations for method 300 is possible. For example, at a certain point in the hybrid pyrosequencing process where near 100% certainty of the candidate identity has been determined, method 300 may transition to a directed sequencing approach. In the directed sequencing approach, the candidate sequence is known and the exact nucleotides are dispensed in the known order to determine whether the specific sequence is present or not. Direct sequencing may be used to confirm the identity of the candidate.

In another example, at a certain point in the hybrid pyrosequencing process where all candidate sequences in the library of possible results have been excluded, method 300 may transition to a de novo sequencing approach. In the de novo sequencing approach, the nucleotides (A, G, C, and T) are added in a pre-determined order to determine the unknown sequence.

In yet another example, at a certain point in the hybrid pyrosequencing process where all candidate sequences in the library of possible results have been excluded, method 300 may query (e.g., via the Internet) another database and/or a larger database to continue with the hybrid pyrosequencing approach.

In yet another example, at a certain point in the hybrid pyrosequencing process multiple nucleotides (e.g., two or three nucleotides) may be dispensed simultaneously to potentially reduce the library of candidate sequences as much as possible process. For example, a database of candidate sequences may include four possibilities for the next two bases in the de novo sequence:

(1) ATC
(2) ATG
(3) ACC
(4) CTC

Two bases, A and T, may be dispensed together. If A and T are incorporated, as indicated by a double peak, candidate sequences (3) and (4) may be excluded from the search space. If only A is incorporated, as indicated by a single peak, candidate sequences (1), (2), and (4) may be excluded from the search space.

In yet another example, the order of nucleotide dispensation may be selected to distinguish similar organisms (sequences) in a sample. For example, a sample includes two organisms where at a certain position one sequence has AA and the other sequence has A. The sequencing program would show a 3X peak. To determine the distribution of the 3X signal for A, a database of candidate sequences may be queried for the most probable nucleotide to follow AA and the most probable nucleotide to follow A. If the most probable nucleotide to follow AA is G, and the most probable nucleotide to follow A is T, then G may be dispensed, followed by T. The expected result would be 2 1X peaks. Further sequencing would provide further confirmation.

6.1.1 Examples

Selection of a nucleotide to be dispensed in a pyrosequencing reaction may be based in part on comparison of a de novo sequence with a database of non-sequence parameters and in part on frequency of a nucleotide in a database of possible candidate sequences. Non-sequence parameters may include, but are not limited to, selection criteria, such as incidence of infection and diagnostic symptoms. For example, a database of incidence of infection may include a plurality of infectious agents (e.g., bacterial, fungal and/or viral) associated with a certain probability of infection. The database may also include nucleic acid sequences of the organisms stored in the database (i.e., candidate sequences). A database of diagnostic symptoms may, for example, include a plurality of symptomatic information associated with a plurality of infectious agents (e.g., bacterial, fungal, and/or viral).

In one example, the selection of a particular nucleotide is based in part on incidence of infection data and in part on frequency of a nucleotide in a database of candidate sequences. For example, an incidence of infection database may include four bacteria species A, B, C and D with the following sequences and incidence of infection:

A. CTGT—incidence is low
B. CGGT—incidence is low
C. CTTT—incidence is low
D. TGCC—incidence is very high An example of a method of selecting a nucleotide for dispensation based in part on incidence data and in part on frequency of a nucleotide in a database of candidate sequences may include, but is not limited to, the following steps.

In one step, T is dispensed based on the very high incidence of infection associated with bacteria D. If T is incorporated, the search space is limited to any sequences associated with bacteria D. If T is not incorporated, the search space is limited to any sequences associated with bacteria A, B, and C.

In another step, a database of candidate sequences is queried. In one example, a database of candidate sequences may be included as part of a database of incidence of infection. In another example, the database of candidate sequences may be a separate database. If T is incorporated in the step above, candidate sequences for bacteria D are examined. The choice of dispensation is made to decrease the library of candidate sequences as much as possible. For example, if three possible sequences are associated with bacteria D and of these three, two begin with T and one begins with C, C is dispensed. If T is not incorporated in the step above, candidate sequences for bacteria A, B, and C are examined.

In another example, the selection of one or more nucleotides is based solely on incidence of infection data to the extent that such data provides a useful selection criterion, and then when incidence of infection data is no longer useful, selection is based on nucleotide frequency in a database of candidate sequences.

In another example, the selection of a particular nucleotide is based in part on diagnostic data and in part on frequency of a nucleotide in a database of candidate sequences. In this example, a database of diagnostic symptoms that includes a plurality of symptomatic information associated with a plurality of infectious agents (e.g., bacterial, fungal, and/or viral) may be queried to initiate the pyrosequencing reaction.

In another example, the selection of a particular nucleotide is based in part on diagnostic data and incidence of infection data and in part on frequency of a nucleotide in a database of candidate sequences.

In yet another example, the selection process may include an algorithm that determines whether incidence data/diagnostic data or frequency in a database has the strongest predictive value, and then selects the nucleotide based on the strongest predictive value.

6.2 Droplet-Based Pyrosequencing

The invention provides devices, systems and methods for hybrid pyrosequencing on a droplet actuator.

Figure 4:
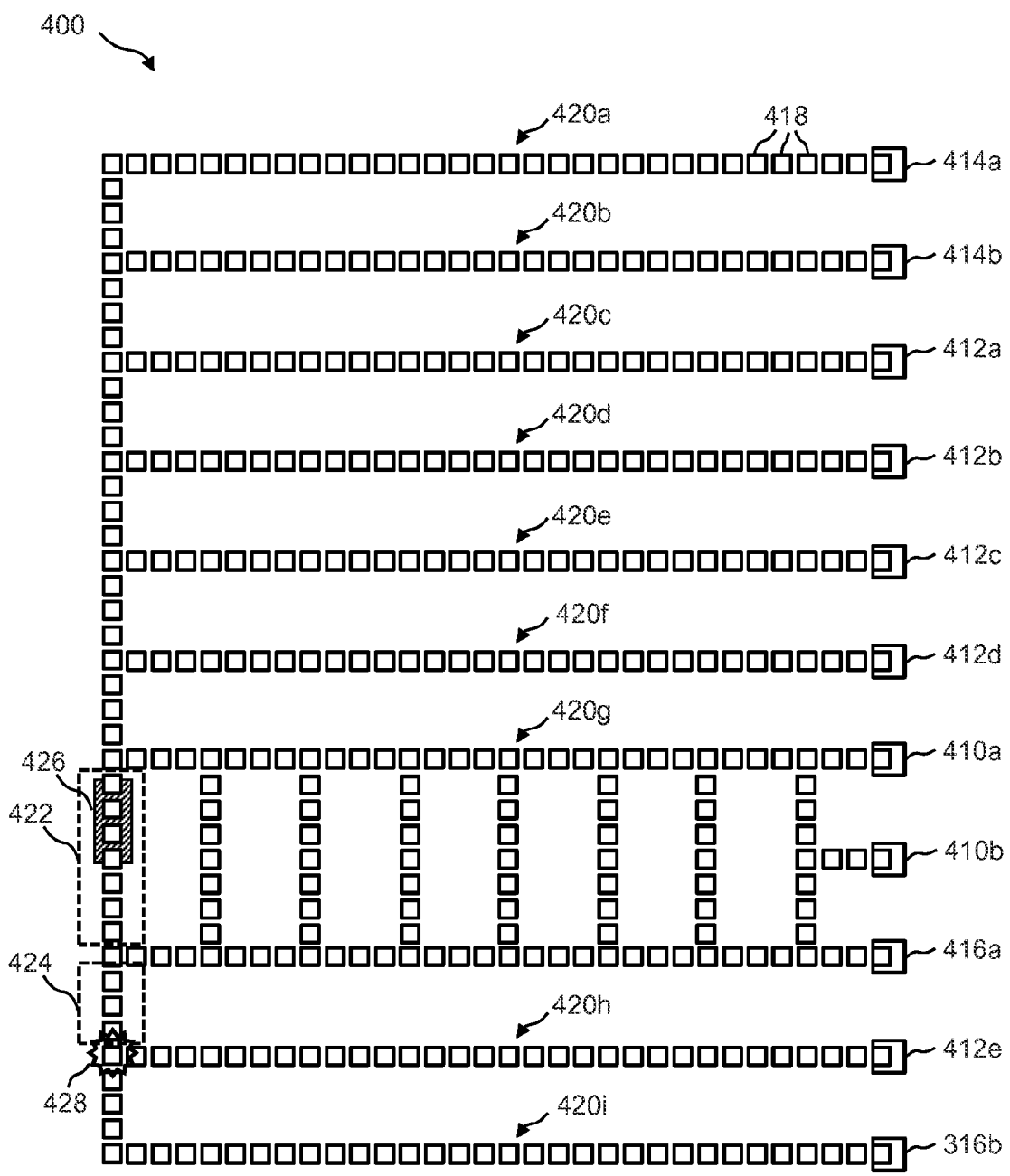
FIG. 4 illustrates a top view of an example of an electrode arrangement of an embodiment of a droplet actuator exemplifying certain aspects of the invention.

FIG. 4 illustrates a top view of an example of an electrode arrangement 300 of an embodiment of a droplet actuator exemplifying certain aspects of the invention. Dedicated electrode lanes provide transport of nucleotide base droplets to a reactor lane. The use of dedicated lanes for nucleotide base droplets minimizes cross-contamination among nucleotides. A dedicated electrode lane provides transport of enzyme mix directly onto the detection electrode. Using a dedicated electrode lane for enzyme mix reduces enzyme deposition on the wash lanes. Reduction of enzyme contamination permits the start of the sequencing reaction to be precisely controlled.

Electrode arrangement 300 includes multiple dispensing electrodes, which may, for example, be allocated as sample dispensing electrodes 310a and 310b for dispensing sample fluids (e.g., DNA immobilized on magnetically responsive beads); reagent dispensing electrodes 312, i.e., reagent dispensing electrodes 312a through 312e, for dispensing different reagent fluids (e.g., dATPαs, dCTP, dGTP, dTTP, enzyme mix); wash buffer dispensing electrodes 314a and 314b for dispensing wash buffer fluids; and waste collection electrodes 316a and 316b for receiving spent reaction droplets. Sample dispensing electrodes 310, reagent dispensing electrodes 312, wash buffer dispensing electrodes 314, and waste collection electrodes 316 are interconnected through an arrangement, such as a path or array, of droplet operations electrodes 318. A path of droplet operations electrodes 318 extending from each dispensing and collection electrodes forms dedicated electrode lanes 320, i.e., dedicated electrode lanes 320a through 320i.

Electrode arrangement 300 may include a washing zone 322 and a reaction zone 324. A magnet 326 is located in close proximity to wash lane 322. Magnet 326 may be embedded within the deck that holds the droplet actuator when the droplet actuator is mounted on the instrument (not shown). Magnet 326 is positioned in a manner which ensures spatial immobilization of nucleic acid-attached beads during washing between the base additions. Mixing may be performed in reactor zone 324 away from magnet 326. The positioning of the wash dispensing electrodes 314 and waste collection electrodes 316 improves washing efficiency and reduces time spent in washing. A detection spot 328 is positioned in proximity of reactor zone 324.

A variety of pyrosequencing protocols may be executed using electrode arrangement 300 of the invention. An example of a three-enzyme pyrosequencing protocol is as follows. A PCR amplified DNA template hybridized to a sequencing primer may be coupled to magnetically responsive beads. A droplet of the beads suspended in wash buffer may be combined with a droplet of one of the four nucleotides mixed with APS and luciferin in wash buffer. A droplet containing all three enzymes (DNA polymerase, ATP sulfurylase and luciferase) may be combined with the bead and nucleotide-containing droplet. The resulting droplet may be mixed and transported to the detector location. Incorporation of the nucleotide may be detected as a luminescent signal proportional to the number of adjacent bases incorporated into the strand being synthesized, or as a background signal for a non-incorporated (mismatch) nucleotide. After the reaction is complete, the beads may be transported to the magnet and washed. Washing may be accomplished by addition and removal of wash buffer while retaining substantially all beads in the droplet. This entire sequence constitutes one full pyrosequencing cycle which may be repeated multiple times with the sequence of nucleotide additions determined in real-time.

In a specific example, a PCR amplified DNA template hybridized to a sequencing primer may be coupled to 2.8 µm diameter magnetically responsive beads. A 2X (800) nL droplet of the beads suspended in wash buffer may be dispensed and combined with a 1X (400 nL) droplet of one of the four nucleotides mixed with APS and luciferin in wash buffer. Selection of a nucleotide to be dispensed may, for example, be based in part on non-sequence parameters (e.g., incidence of infection and/or diagnostic symptoms) and/or in part on frequency of a nucleotide in a database of possible candidate sequences. In one example, at least the first nucleotide to be dispensed is selected based on a query of a database(s) of non-sequence parameters (e.g., incidence of infection, diagnostic symptoms) and subsequent dispensations determined based on a comparison of the de novo sequence and the library of possible results (e.g., candidate sequences). A 1X (400 nL) droplet containing all three enzymes (DNA polymerase, ATP sulfurylase and luciferase) may be combined with the beads and nucleotides resulting in a 4X (1600 nL) reaction volume. The 4X droplet may be mixed and transported to the detector location. Incorporation of the nucleotide may be detected as a luminescent signal proportional to the number of adjacent bases incorporated into the strand being synthesized, or as a background signal for a non-incorporated (mismatch) nucleotide. After the reaction is complete the beads may be transported to the magnet and washed by addition and removal of wash buffer finally resulting in the 1600 nL of reaction mix being replaced by 800 nL of fresh wash buffer while essentially all of the beads may be retained in the droplet. This entire sequence constituted one full pyrosequencing cycle which may be repeated multiple times with the sequence of nucleotide additions determined in real-time as described in reference to FIG. 3. In the above protocol, "X" refers to the number of unit-sized droplets contained in the volume. A unit droplet is approximately the smallest volume that can be handled based on the size of the individual electrodes.

6.3 Example Applications

The nucleic acid sequencing systems and methods of the invention are useful in a variety of settings including medical diagnostics. Rapid and accurate diagnosis of infectious disease is crucial both for the effective management of disease in individual patients and for ameliorating the public health problems of multi-drug resistant pathogens and community acquired infections.

In one embodiment, the systems and methods of the invention may be used to rapidly and efficiently identify and type human immunodeficiency (HIV) virus. One of the obstacles to effective treatment of HIV is its high genetic variability that is associated with resistance to antiretroviral therapies. Rapid identification of HIV and accurate subtyping of the virus is crucial for effective management of the disease. HIV subtyping may, for example, be performed using reverse transcriptase-polymerase chain reaction (RT-PCR) amplification of viral RNA and hybrid pyrosequencing. Selection of a nucleotide to be dispensed in a pyrosequencing reaction to subtype HIV may be based in part on comparison of a de novo sequence with a database of non-sequence parameters and in part on frequency of a nucleotide in a database of possible candidate sequences (i.e., HIV sequences). The database of non-sequence parameters may, for example, be a database of incidence of infection of HIV viral subtypes. The database of non-sequence parameters may be queried to select the next nucleotide to be dispensed to the extent that such data provides a useful selection criterion, and then when non-sequence parameter data is no longer useful, selection is based on nucleotide frequency in a database of candidate viral sequences.

In another embodiment, the systems and methods of the invention may be used to rapidly and efficiently identify and type methicillin-resistant *Staphylococcus aureus* (MRSA). MRSA is a significant cause of healthcare- and community-associated infections, and its prevalence continues to increase. Currently, increasing numbers of community-acquired MRSA (CA-MRSA) strains are appearing that are able to cause severe infections in otherwise healthy people. High-level resistance to methicillin is caused by the mecA gene. The mecA regulon (mecA, mec1, and mecR1) is carried by a mobile genetic element designated staphylococcal cassette chromosome mec (SCCmec). SCCmec also includes the ccr gene complex and J regions (junkyard, J1, J2, and J3). Variations in the J regions may be used for defining SCCmec subtypes. MRSA typing may, for example, be performed using PCR amplification of bacterial DNA and hybrid pyrosequencing. In one example, selection of at least a first nucleotide to be dispensed in a pyrosequencing reaction to type MRSA may be based on a database of incidence of infection of MRSA types (non-sequence parameters). The database of non-sequence parameters may be queried to select the next nucleotide to be dispensed to the extent that such data provides a useful selection criterion, and then when non-sequence parameter data is no longer useful, selection is based on nucleotide frequency in a database of candidate MRSA sequences.

In yet another embodiment, the systems and methods of the invention may be used to rapidly and efficiently identify and type influenza A viruses. Influenza A viruses circulate worldwide and cause annual epidemics of human respiratory illness. Influenza A viruses are classified by subtype on the basis of the two main surface glycoproteins hemagglutinin (HA) and neuraminidase (NA). Different subtypes (e.g., H1N1 and H3N2) may be in circulation among human populations at different times. Influenza A viruses are further characterized into strains. Because influenza viruses are dynamic and constantly evolving, new strains continually appear. Rapid and accurate subtyping of the influenza A virus is important for effective management of the flu and timely development of appropriate anti-flu vaccines. Genotyping influenza A viruses may be based on polymorphisms in HA and/or NA coding regions or internal viral gene sequences. In one example, influenza A subtyping maybe performed using RT-PCR amplification of one or more internal gene sequences (e.g., NS, M, NP, PA, PB1, or PB2 genes) and hybrid pyrosequencing. Selection of at least a first nucleotide to be dispensed in a pyrosequencing reaction to subtype influenza A may be based on a database of incidence of infection of influenza A types (non-sequence parameter data). The database of incidence of infection of influenza A types may be queried to select the next nucleotide to be dispensed to the extent that such data provides a useful selection criterion, and then when non-sequence parameter data is no longer useful, selection is based on nucleotide frequency in a database of candidate influenza A sequences.

In yet another embodiment, the systems and methods of the invention may be used to rapidly and efficiently determine the sequences of known and unknown organisms (e.g., infectious agents) in complex environmental samples (e.g., food, water, air). An identification strategy may, for example, be based on the premise that sequencing the conserved ancient elements of the replicative machinery, such as a 1,500 base sequence of the 16S and 28S ribosomal DNA (rDNA) sequences, may be used to identify most bacterial and fungal pathogens, respectively. Sequencing of the variable regions of the 16S and 28S rDNA is widely accepted as the most robust and versatile method for identification of microbes in a complex environment where there are mixtures of organisms. The sequences that flank the variable regions of the 16S rDNA sequences in bacteria and 28S rDNA in fungi are highly conserved and may be used to amplify the variable regions of the sequences from all organisms, both known and unknown. These sequences show a great degree of homology in related organisms and may be used to make taxonomic identification. In one example, genomic DNA is isolated from a complex mixture of organisms in an environmental sample, such as a water sample. The genomic DNA is amplified using specific primers that flank the 16s (bacterial) and 28s rDNA (fungal) variable sequences. Selection of at least a first nucleotide to be dispensed in a pyrosequencing reaction to identify the organisms in the sample may, for example, be based on a database of incidence of contamination that includes a plurality of infectious agents (e.g., bacterial and fungal) typically associated with a sample source (e.g., a water sample). The database of incidence of contamination may be queried to select the next nucleotide to be dispensed to the extent that such data provides a useful selection criterion, and then when incidence of contamination data is no longer useful, selection is based on nucleotide frequency in a database of candidate bacterial and fungal sequences. If at a certain point in the hybrid pyrosequencing process where all candidate sequences in the databases of candidate bacterial and fungal sequences have been excluded, hybrid pyrosequencing may transition to a de novo sequencing approach. In the de novo sequencing approach, the nucleotides (A, G, C, and T) are added in a pre-determined order to determine the unknown sequence.

6.4 Systems

It will be appreciated that various aspects of the invention may be embodied as a method, system, computer readable medium, and/or computer program product. Aspects of the invention may take the form of hardware embodiments, software embodiments (including firmware, resident software, micro-code, etc.), or embodiments combining software and hardware aspects that may all generally be referred to herein as a "circuit," "module" or "system." Furthermore, the methods of the invention may take the form of a computer program product on a computer-usable storage medium having computer-usable program code embodied in the medium.

Any suitable computer useable medium may be utilized for software aspects of the invention. The computer-usable or computer-readable medium may be, for example but not limited to, an electronic, magnetic, optical, electromagnetic, infrared, or semiconductor system, apparatus, device, or propagation medium. The computer readable medium may include transitory and/or non-transitory embodiments. More specific examples (a non-exhaustive list) of the computer-readable medium would include some or all of the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission medium such as those supporting the Internet or an intranet, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device.

Program code for carrying out operations of the invention may be written in an object oriented programming language such as Java, Smalltalk, C++ or the like. However, the program code for carrying out operations of the invention may also be written in conventional procedural programming languages, such as the "C" programming language or similar programming languages. The program code may be executed by a processor, application specific integrated circuit (ASIC), or other component that executes the program code. The program code may be simply referred to as a software application that is stored in memory (such as the computer readable medium discussed above). The program code may cause the processor (or any processor-controlled device) to produce a graphical user interface ("GUI"). The graphical user interface may be visually produced on a display device, yet the graphical user interface may also have audible features. The program code, however, may operate in any processor-controlled device, such as a computer, server, personal digital assistant, phone, television, or any processor-controlled device utilizing the processor and/or a digital signal processor.

The program code may locally and/or remotely execute. The program code, for example, may be entirely or partially stored in local memory of the processor-controlled device. The program code, however, may also be at least partially remotely stored, accessed, and downloaded to the processor-controlled device. A user's computer, for example, may entirely execute the program code or only partly execute the program code. The program code may be a stand-alone software package that is at least partly on the user's computer and/or partly executed on a remote computer or entirely on a remote computer or server. In the latter scenario, the remote computer may be connected to the user's computer through a communications network.

The invention may be applied regardless of networking environment. The communications network may be a cable network operating in the radio-frequency domain and/or the Internet Protocol (IP) domain. The communications network, however, may also include a distributed computing network, such as the Internet (sometimes alternatively known as the "World Wide Web"), an intranet, a local-area network (LAN), and/or a wide-area network (WAN). The communications network may include coaxial cables, copper wires, fiber optic lines, and/or hybrid-coaxial lines. The communications network may even include wireless portions utilizing any portion of the electromagnetic spectrum and any signaling standard (such as the IEEE 802 family of standards, GSM/CDMA/TDMA or any cellular standard, and/or the ISM band). The communications network may even include powerline portions, in which signals are communicated via electrical wiring. The invention may be applied to any wireless/wireline communications network, regardless of physical componentry, physical configuration, or communications standard(s).

Certain aspects of invention are described with reference to various methods and method steps. It will be understood that each method step can be implemented by the program code and/or by machine instructions. The program code and/or the machine instructions may create means for implementing the functions/acts specified in the methods.

The program code may also be stored in a computer-readable memory that can direct the processor, computer, or other programmable data processing apparatus to function in a particular manner, such that the program code stored in the computer-readable memory produce or transform an article of manufacture including instruction means which implement various aspects of the method steps.

The program code may also be loaded onto a computer or other programmable data processing apparatus to cause a series of operational steps to be performed to produce a processor/computer implemented process such that the program code provides steps for implementing various functions/acts specified in the methods of the invention.

7 CONCLUDING REMARKS

The foregoing detailed description of embodiments refers to the accompanying drawings, which illustrate specific embodiments of the invention. Other embodiments having different structures and operations do not depart from the scope of the invention. The term "the invention" or the like is used with reference to certain specific examples of the many alternative aspects or embodiments of the applicants' invention set forth in this specification, and neither its use nor its absence is intended to limit the scope of the applicants' invention or the scope of the claims. This specification is divided into sections for the convenience of the reader only. Headings should not be construed as limiting of the scope of the invention. The definitions are intended as a part of the description of the invention. It will be understood that various details of the invention may be changed without departing from the scope of the invention. Furthermore, the foregoing description is for the purpose of illustration only, and not for the purpose of limitation.

What is claimed:

1. A method for identifying a nucleic acid sequence in a sample by hybrid pyrosequencing, the method comprising:
   (a) selecting a nucleotide to be dispensed to a sample comprising a primed DNA template and reagents sufficient for sequencing-by-synthesis of a de novo nucleic acid sequence to be identified, wherein selecting comprises querying a database of non-sequence parameters and/or comparing the de novo sequence to a library of candidate sequences, further wherein the query of the database of non-sequence parameters comprises using an algorithm to determine whether the non-sequence parameters comprising incidence of infection and organism type or diagnostic symptoms and organism type, or frequency of the nucleotide in the library of candidate sequences has the strongest predictive value, and selecting the nucleotide based on the strongest predictive value;
   (b) controlling a dispenser to dispense the selected nucleotide to the sample;
   (c) detecting a response signal to the dispensation;
   (d) determining whether the dispensed nucleotide was incorporated or not incorporated;
   (e) repeating steps (a)-(d) in response to determining that the dispensed nucleotide was not incorporated;
   (f) in response to determining that the dispensed nucleotide was incorporated: (i) comparing the de novo sequence to the library of candidate sequences; and (ii) excluding candidate sequences that do not match the de novo sequence; and
   (g) repeating steps (a)-(f) until the de novo sequence is uniquely identified, wherein a sequence and/or nonsequence parameter database is queried during each reaction cycle.

2. The method of claim 1, further comprising using a droplet actuator to implement steps (a)-(c),
   (a) wherein step (b) further comprises controlling the dispenser to dispense:
      (i) a first droplet comprising the primed DNA template immobilized on a bead;
      (ii) a second droplet comprising the selected nucleotide and detection reagents; and
      (iii) a third droplet comprising enzyme reagents;
   (b) wherein the method further comprises on the droplet actuator:
      (i) combining the first, second, and third droplets;
      (ii) transporting the combined droplet to a detector location; and
      (iii) transporting the droplets to a washing location for wash of the beads prior to returning to step (b).

3. The method of claim 2, wherein the detection reagents comprise adenosine 5' phosphosulfate and luciferin, and the enzyme reagents comprise DNA polymerase, ATP sulfurylase, and luciferase.

4. The method of claim 2, wherein the bead is a magnetically responsive bead.

5. The method of claim 1, wherein identification of the nucleic acid sequence in the sample identifies one or more organisms in the sample.

6. The method of claim 5, wherein the organism is a bacteria, virus, or fungi.

7. The method of claim 1, wherein identification of the nucleic acid sequence in the sample rules out one or more organisms in the sample.

8. The method of claim 1, wherein identification of the nucleic acid sequence in the sample determines the nucleotide sequence of an unknown organism in the sample.

9. The method of claim 1, wherein the sample is a biological sample or an environmental sample.

10. The method of claim 1, wherein the nucleic acid sequence is a human immunodeficiency virus (HIV) sequence, a methicillin-resistant *Staphylococcus aureus* (MRSA) sequence, an influenza A sequence, or a 16S or 28S ribosomal DNA sequence of a known or an unknown organism.

11. The method of claim 1, wherein the database of non-sequence parameters comprises one or more of source of the sample, incidence of infection and organism type, or diagnostic symptoms and organism type.

12. The method of claim 1, wherein the selecting of a first nucleotide to be dispensed is based in part on the query of a database of non-sequence parameters and in part on frequency of the nucleotide in the library of candidate sequences.

13. The method of claim 1, wherein the selecting of the nucleotide to be dispensed, subsequent to a first nucleotide to be dispensed, is based on the comparison of the de novo sequence to the library of candidate sequences to select a most probable nucleotide for that position and to decrease the library of candidate sequences.

14. The method of claim 1, further comprising transitioning to a directed sequencing approach wherein the de novo sequence is uniquely identified to near 100% certainty, the direct sequencing approach comprising dispensing the nucleotide to the sample in an order dictated by the de novo sequence uniquely identified to near 100% certainty.

15. The method of claim 1, further comprising transitioning to a de novo sequencing approach in response to all the candidate sequences in the library of candidate sequences being excluded, the de novo sequencing approach comprising dispensing the nucleotides A, G, C, and T to the sample in a predetermined order to identify the nucleotide sequence.

16. The method of claim 1, further comprising querying an additional database of candidate sequences in response to all the candidate sequences in the library of candidate sequences being excluded.

17. The method of claim 1, further comprising:
   (a) selecting multiple nucleotides; and
   (b) dispensing the multiple nucleotides simultaneously to reduce the library of candidate sequences.

18. The method of claim 17, wherein multiple nucleotides are 2 or 3 nucleotides.

19. The method of claim 17, wherein step (a) further comprises distinguishing between a first similar sequence and a second similar sequence in the library of candidate sequences based on a determination of the most probable nucleotide to follow in each of the first similar sequence and the second similar sequence.

* * * * *